US010475177B2

(12) United States Patent
Kurahashi et al.

(10) Patent No.: US 10,475,177 B2
(45) Date of Patent: Nov. 12, 2019

(54) METHOD OF INSPECTING SURFACE OF CERAMIC BODY

(71) Applicant: NGK INSULATORS, LTD., Nagoya (JP)

(72) Inventors: Ryota Kurahashi, Nagoya (JP); Akihiro Mizutani, Ichinomiya (JP); Takafumi Terahai, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 15/696,708

(22) Filed: Sep. 6, 2017

(65) Prior Publication Data

US 2017/0365050 A1    Dec. 21, 2017

Related U.S. Application Data

(63) Continuation of application No. PCT/JP2016/078670, filed on Sep. 28, 2016.

(30) Foreign Application Priority Data

Oct. 6, 2015 (JP) .................................. 2015-198545

(51) Int. Cl.
*G06K 9/00* (2006.01)
*G06T 7/00* (2017.01)
(Continued)

(52) U.S. Cl.
CPC ............ *G06T 7/0008* (2013.01); *G01B 11/30* (2013.01); *G01N 21/8806* (2013.01);
(Continued)

(58) Field of Classification Search
None
See application file for complete search history.

(56) References Cited

U.S. PATENT DOCUMENTS

| 8,090,143 B2 | 1/2012 | Komaki et al. |
| 2003/0184740 A1* | 10/2003 | Paradis .............. G01N 21/8806 356/237.1 |
| 2011/0128370 A1 | 6/2011 | Booth et al. |

FOREIGN PATENT DOCUMENTS

| EP | 3 088 874 A1 | 11/2016 |
| JP | S52-49856 | 4/1977 |

(Continued)

OTHER PUBLICATIONS

Namuta Monetoshi, Translation of JP 2002-168971,Inspection Device using Multi-Illumination, Obtained by Japanese Platform for Patent Information, Date Published: Jun. 14, 2002, Date accessed online Feb. 7, 2019, Cited by applicant in IDS submitted on Jan. 23, 2019. (Year: 2002).*

(Continued)

*Primary Examiner* — Tahmina N Ansari
(74) *Attorney, Agent, or Firm* — Burr & Brown, PLLC

(57) ABSTRACT

An inspection method for a surface of a ceramic body capable of determining any crack more reliably than conventionally done is provided. The method includes a step of performing image capturing of an illuminated region of an inspection surface being illuminated with at least one of first and second illumination light from mutually different directions sandwiching an image capturing means, a step of generating a determination image, and a step of performing determination. When a first determination image is generated based on a first image capturing result obtained under illumination at least with the first illumination light, and a second determination image is generated based on a second image capturing result under illumination at least with the second illumination light, those images are generated so that determination of the presence or absence of any crack can be (Continued)

performed based on a difference between formation manners of shadow regions in those images.

24 Claims, 9 Drawing Sheets

(51) Int. Cl.
*G01B 11/30* (2006.01)
*G01N 21/95* (2006.01)
*G06T 7/90* (2017.01)
*G01N 21/88* (2006.01)
*H04N 5/225* (2006.01)

(52) U.S. Cl.
CPC ............. *G01N 21/95* (2013.01); *G06T 7/001* (2013.01); *G06T 7/0004* (2013.01); *G06T 7/90* (2017.01); *G06T 2207/10016* (2013.01); *G06T 2207/10024* (2013.01); *G06T 2207/10152* (2013.01); *G06T 2207/30108* (2013.01); *G06T 2207/30172* (2013.01); *H04N 5/2256* (2013.01)

(56) References Cited

FOREIGN PATENT DOCUMENTS

| | | |
|---|---|---|
| JP | 09-257671 A1 | 10/1997 |
| JP | 2002-168791 | 6/2002 |
| JP | 2009-109243 | 5/2009 |
| JP | 2010-078562 A1 | 4/2010 |
| JP | 2011-117788 A1 | 6/2011 |
| WO | 2007/105825 A1 | 9/2007 |
| WO | 2013/008789 A1 | 1/2013 |
| WO | 2014/188457 | 11/2014 |
| WO | 2015/098929 A1 | 7/2015 |

OTHER PUBLICATIONS

International Search Report and Written Opinion (PCT/JP2016/078670) dated Dec. 6, 2016.
English translation of International Preliminary Report on Patentability (Application No. PCT/JP2016/078670) dated Apr. 19, 2018.
Japanese Office Action (and English translation from Global Dossier) from a corresponding Japanese patent application (JP 2017-520556) dated Jan. 22, 2019, 9 pages.
Japanese Office Action (Application No. 2017-520556) dated Jul. 30, 2019 (with English translation).

* cited by examiner

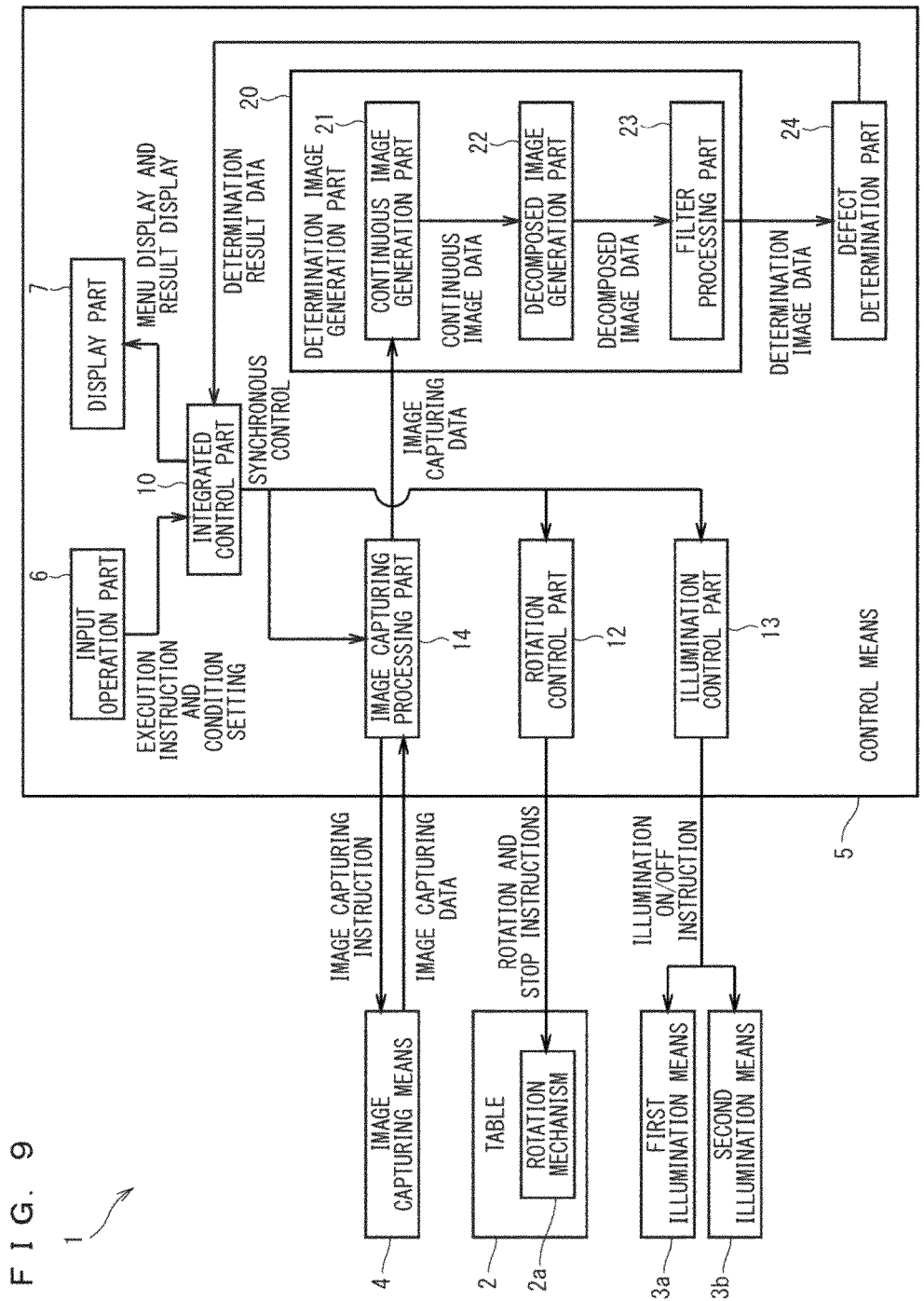
F I G. 9

METHOD OF INSPECTING SURFACE OF CERAMIC BODY

TECHNICAL FIELD

The present invention relates to a method that inspects the surface of a ceramic body, and particularly relates to a method that detects any crack formed on the surface of a ceramic body manufactured by an extrusion molding method.

BACKGROUND ART

A ceramic honeycomb structural body has been widely used as a filter that traps a particulate matter included in exhaust gas from, for example, an internal combustion or a boiler, or a catalyst carrier of an exhaust gas purification catalyst. The honeycomb structural body is a tubular (for example, cylindrical) structural body whose both ends are open and which includes inside what is called a honeycomb structure (honeycomb construction). In other words, the honeycomb structural body includes a plurality of cells in the inside thereof surrounded by a tubular outer surface (outer wall), the plurality of cells being partitioned by a partition and each being aligned with an axial direction of the structural body. The ceramic honeycomb structural body, which is excellent in thermal resistance, thermal shock resistance, and oxidation resistance, provides wide usage in addition to the above-described usages.

Typically, the ceramic honeycomb structural body is manufactured by shaping, by an extrusion molding method, a clay body obtained through mixing of ceramic (for example, alumina) powder as a component material thereof together with organic binder, water and the like to obtain a honeycomb compact, and then by firing the honeycomb compact thus obtained.

However, when the honeycomb structural body is manufactured by this method, some defects such as occurrence of a crack on the outer wall of the honeycomb structural body and adhesion of a foreign substance to the outer wall may occur. The occurrence of a crack and the adhesion of a foreign substance potentially cause, for example, reduction in the strength of the honeycomb structural body, reduction in filtering performance when the honeycomb structural body is used as a filter, reduction in exhaust-gas purification performance when the honeycomb structural body is used as a catalyst carrier. Thus, inspection of the presence or absence of these defects needs to be performed before using the honeycomb structural body. Technologies for such defect inspection have been publicly known (for example, refer to Patent Documents 1 to 3).

Among these technologies, Patent Documents 1 and 2 each disclose a method of performing image capturing of the surface of an outer wall, as a side surface, of a cylinder honeycomb structural body being rotated about a central axis thereof, and inspecting any defect on the outer wall based on a result of the image capturing The existence of a defect as described above affects a characteristic of the honeycomb structural body, and thus the defect inspection is important to maintain the quality of the honeycomb structural body. In particular, when the cylindrical honeycomb structural body is manufactured as a ceramic fired body by firing a honeycomb compact obtained through extrusion shaping, a crack is likely to be formed along the axial direction of the honeycomb structural body, and it is required to excellently detect the crack of that kind.

On the other hand, in the cylindrical honeycomb structural body as a ceramic fired body, an undulation (surface relief) exists along a circumferential direction on the outer wall thereof in some cases. This undulation does not affect the quality and characteristic of the honeycomb structural body, and thus the existence thereof is allowed.

However, there is such a problem that, when the defect inspection is performed by, for example, the methods disclosed in Patent Documents 1 and 2, what is called over-detection (excessive detection) occurs that an undulation, which does not need to be determined as a defect, is detected as a defect.

In particular, a shadow formed at a crack extending in the axial direction of the honeycomb structural body and a shadow formed at a recess formed in the axial direction of the honeycomb structural body due to a generated undulation are similar, and the over-detection of the latter as the former is likely to occur.

Visual inspection has a high crack detection reliability but takes a long inspection time, and thus is disadvantageous in production efficiency and cost.

PRIOR ART DOCUMENTS

Patent Documents

Patent Document 1: WO 2007/105825
Patent Document 2: U.S. Patent Application Specification No. 2011/0128370
Patent Document 3: Japanese Patent Application Laid-Open No. 09-257671

SUMMARY OF INVENTION

The present invention is intended to solve the above-described problem and provide a surface inspecting method capable of more reliably determining the presence or absence of any crack formed on a surface of a ceramic body than conventionally done.

In a first aspect of the present invention, a method of examining a crack for a surface of a ceramic body includes: an image capturing step of performing, through a predetermined image capturing means, image capturing of a predetermined illuminated region of an inspection surface which is a partial surface of the ceramic body, said illuminated region being illuminated with at least one of first illumination light and second illumination light; a determination image generation step of generating, based on an image capturing result in the image capturing step, a determination image that is usable for determination of the presence or absence of any crack; and a determination step of determining the presence or absence of any crack on the inspection surface based on the determination image. The first and second illumination light is emitted to the inspection surface from mutually different directions sandwiching the image capturing means. In the image capturing step, image capturing of the illuminated region is performed under illumination with at least one of the first and second illumination light. When a first image capturing result is defined as an image capturing result obtained by performing image capturing of the inspection surface with the image capturing means under illumination at least with the first illumination light, a second image capturing result is defined as an image capturing result obtained by performing image capturing of the inspection surface with the image capturing means under illumination at least with the second illumination light, and in the determination image generation step, a first determination image is generated based on the first image capturing result, and a second determination image is generated based on the second image capturing result, the first and second determination images are generated so that determination of the presence or absence of any crack on the inspection surface can be performed based on a difference between formation manners of shadow regions in the first and second determination images when the first and second determination images are compared with each other, and in the determination step, the presence or absence of any crack on the inspection surface is determined based on the first and second determination images.

In a second aspect of the present invention, in the inspection method for the surface of the ceramic body according to the first aspect, in the determination image generation step, the first determination image is generated, based on the first image capturing result, as an image including only an image formation signal for a first color component, or as an image including an image formation signal for the first color component and an image formation signal for a color component other than for the first color component, having a signal amount smaller than a predetermined threshold, and the second determination image is generated, based on the second image capturing result, as an image including only an image formation signal for a second color component, or as an image including an image formation signal for the second color component and an image formation signal for a color component other than the second color component, having a signal amount smaller than a predetermined threshold.

In a third aspect of the present invention, in the inspection method for the surface of the ceramic body according to the second aspect, in the image capturing step, a result of image capturing with the image capturing means is generated as image capturing data in a predetermined data format, the determination image generation step is a determination image data generation step of generating determination image data which is image data of the determination image by acquiring a pixel value for a predetermined color component, as an image formation signal for the predetermined color component, from the image capturing data, and in the determination image data generation step, a first determination image data which is image data of the first determination image is generated based on first image capturing data generated as the first image capturing result, and a second determination image data which is image data of the second determination image is generated based on second image capturing data generated as the second image capturing result.

In a fourth aspect of the present invention, in the inspection method for the surface of the ceramic body according to the third aspect, in the image capturing step, a result of image capturing with the image capturing means is generated as image capturing data in a data format in which a pixel value for each of a plurality of color components is independently described, and in the determination image data generation step, the first determination image data is generated by acquiring, from first image capturing data generated as the first image capturing result, only a pixel value for the first color component, or a pixel value for the first color component and a pixel value for a color component other than the first color component, which is smaller than a predetermined threshold, and the second determination image data is generated by acquiring, from second image capturing data generated as the second image capturing result, a pixel value for the second color component, or a pixel value for the second color component and a pixel value for a color component other than the second color component, which is smaller than a predetermined threshold.

In a fifth aspect of the present invention, in the inspection method for the surface of the ceramic body according to the third aspect, in the image capturing step, a result of image capturing with the image capturing means is generated as image capturing data in a data format in which pieces of pixel value information for a plurality of color components are synthesized, and in the determination image data generation step, the first determination image data in which only a pixel value for the first color component is described, or a pixel value for the first color component and a pixel value for a color component other than the first color component, which is smaller than a predetermined threshold, are described, is generated by decomposing first image capturing data generated as the first image capturing result, and the second determination image data in which only a pixel value for the second color component is described, or a pixel value for the second color component and a pixel value for a color component other than the second color component, which is smaller than a predetermined threshold, are described, is generated by decomposing second image capturing data generated as the second image capturing result.

In a sixth aspect of the present invention, in the inspection method for the surface of the ceramic body according to the third aspect, in the determination step, the presence or absence of any crack on the inspection surface is determined by determining a difference between formation manners of shadow regions in the first and second determination images through comparison of the first and second determination image data, and determination result data in which a result of the determination is described is generated.

In a seventh aspect of the present invention, in the inspection method for the surface of the ceramic body according to the sixth aspect, in the determination step, based on the first and second determination image data, when it is judged a shadow region extending along an identical direction and having a pixel value smaller than a pixel value of a surrounding region exists at identical positions on the inspection surface of the ceramic body in the first and second determination images, and, when it is judged the shadow region exists in either one of the first and second determination images, but a region corresponding to the shadow region does not exist at a formation position of the shadow region nor near the formation position in the other determination image, it is determined that a crack along the identical direction is generated at a place corresponding to the shadow region on the inspection surface of the ceramic body.

In an eighth aspect of the present invention, in the inspection method for the surface of the ceramic body according to the second aspect, a wavelength band of the first illumination light and a wavelength band of the second illumination light are different from each other, in the image capturing step, the first and second image capturing results are acquired as a single image capturing result by performing, with the image capturing means, image capturing of the illuminated region with being illuminated simultaneously with the first and second illumination light, and in the determination image generation step, the first and second determination image data are generated based on the single image capturing result, with setting different wavelength ranges for the first color component and the second color component.

In a ninth aspect of the present invention, in the inspection method for the surface of the ceramic body according to the eighth aspect, the wavelength range for the first color component overlaps at least with the wavelength band of the first illumination light, and the wavelength range for the second color component overlaps at least with the wavelength band of the second illumination light.

In a tenth aspect of the present invention, in the inspection method for the surface of the ceramic body according to the eighth aspect, in the image capturing step, the single piece of image capturing data is obtained by performing image capturing with the image capturing means for a surface parallel to the rotational axis as the inspection surface while the ceramic body is rotated once about a predetermined rotational axis.

In an eleventh aspect of the present invention, in the inspection method for the surface of the ceramic body according to the first aspect, in the determination image generation step, the first determination image is generated based on a brightness signal or a luminance signal in the first image capturing result, and the second determination image is generated based on a brightness signal or a luminance signal in the second image capturing result.

In a twelfth aspect of the present invention, in the inspection method for the surface of the ceramic body according to the eleventh aspect, in the image capturing step, a result of image capturing with the image capturing means is generated as image capturing data in a data format in which a brightness value or a luminance value at each pixel is described, the determination image generation step is a determination image data generation step of generating determination image data which is image data of the determination image by acquiring a brightness value or a luminance value at each pixel from the image capturing data, and in the determination image data generation step, a first determination image data which is image data of the first determination image is generated based on first image capturing data generated as the first image capturing result, and a second determination image data which is image data of the second determination image is generated based on second image capturing data generated as the second image capturing result.

In a thirteenth aspect of the present invention, in the inspection method for the surface of the ceramic body according to the twelfth aspect, in the determination step, the presence or absence of any crack on the inspection surface is determined by determining a difference between formation manners of shadow regions in the first and second determination images through comparison of the first and second determination image data, and determination result data in which a result of the determination is described is generated.

In a fourteenth aspect of the present invention, in the inspection method for the surface of the ceramic body according to the thirteenth aspect, in the determination step, based on the first and second determination image data, when it is judged a shadow region extending along an identical direction and having a pixel value smaller than a pixel value of a surrounding region exists at identical positions on the inspection surface of the ceramic body in the first and second determination images, and when it is judged the shadow region exists in either one of the first and second determination images, but a region corresponding to the shadow region does not exist at a formation position of the shadow region nor near the formation position in the other determination image, it is determined that a crack along the identical direction is generated at a place corresponding to the shadow region on the inspection surface of the ceramic body.

In a fifteenth aspect of the present invention, in the inspection method for the surface of the ceramic body according to the first aspect, in the image capturing step, the first and second image capturing results are obtained by performing, while the ceramic body is rotated about a predetermined rotational axis, image capturing with the image capturing means for a surface parallel to the rotational axis as the inspection surface.

In a sixteenth aspect of the present invention, in the inspection method for the surface of the ceramic body according to the fifteenth aspect, in the image capturing step, the first image capturing result is obtained by performing image capturing of an entirety of the inspection surface with the image capturing means under illumination with the first illumination light while the ceramic body is rotated once about the rotational axis, and then the second image capturing result is obtained by performing image capturing of the entirety of the inspection surface with the image capturing means under illumination with the second illumination light while the ceramic body is additionally rotated once about the rotational axis.

In a seventeenth aspect of the present invention, in the inspection method for the surface of the ceramic body according to the tenth aspect, the ceramic body has a cylindrical shape, and in the image capturing step, the ceramic body is held rotatable in a horizontal plane so that a side surface of the ceramic body is the inspection surface.

In an eighteenth aspect of the present invention, in the inspection method for the surface of the ceramic body according to the tenth aspect aspect, in the image capturing step, image capturing of an entirety of the inspection surface is performed by repeatedly performing image capturing with a predetermined image capturing width, with the image capturing means, of the ceramic body rotating about the rotational axis in a manner that respective image capturing ranges are adjacent to each other or partially overlap with each other, and the first and second image capturing results are obtained by synthesizing a plurality of captured images obtained by the repeated image capturing with the image capturing means.

In a nineteenth aspect of the present invention, in the inspection method for the surface of the ceramic body according to the eighteenth aspect, a line sensor having sensitivity at least to the first and second illumination light is used as the image capturing means.

In a twentieth aspect of the present invention, in the inspection method for the surface of the ceramic body according to the first aspect, an image display step of displaying the first and second determination images on a predetermined image display means to allow determination of the presence or absence of the any crack is further included.

In a twenty-first aspect of the present invention, in the inspection method for the surface of the ceramic body according to the twentieth aspect, in the determination step, the presence or absence of any crack on the inspection surface is determined by determining a difference between formation manners of shadow regions in the first and second determination images through comparison of the first and second determination images displayed on the image display means.

In a twenty-second aspect of the present invention, in the inspection method for the surface of the ceramic body according to the twenty-first aspect, in the determination step, based on the first and second determination images, when it is judged a shadow region extending in an identical direction and darker than a surrounding region exists at identical positions on the inspection surface of the ceramic body in the first and second determination images, and when it is judged the shadow region exists in either one of the first and second determination images, but a region corresponding to the shadow region does not exist at a formation position of the shadow region nor near the formation position in the other determination image, it is determined that a crack along the identical direction is generated at a place corresponding to the shadow region on the inspection surface of the ceramic body.

In a twenty-third aspect of the present invention, in the inspection method for the surface of the ceramic body according to the first aspect, the first illumination light has a wavelength band of 400 nm to 500 nm, and the second illumination light has a wavelength band of 600 nm to 800 nm.

In a twenty-fourth aspect of the present invention, in the inspection method for the surface of the ceramic body according to the first aspect, the first illumination light has a wavelength band of 100 nm to 400 nm, and the second illumination light has a wavelength band of 300 nm to 800 nm.

In a twenty-fifth aspect of the present invention, in the inspection method for the surface of the ceramic body according to the first aspect, the ceramic body is a honeycomb structural body obtained by firing a ceramic compact obtained by extrusion shaping, and a side surface of the honeycomb structural body is the inspection surface.

In a twenty-sixth aspect of the present invention, in the inspection method for the surface of the ceramic body according to the first aspect, the image capturing step and the determination image generation step are performed by a surface inspecting apparatus including a holding part holds that the ceramic body, first illumination means capable of illuminating the predetermined illuminated region of the ceramic body held by the holding part with the first illumination light, second illumination means capable of illuminating the predetermined illuminated region of the ceramic body held by the holding part with the second illumination light, the image capturing means, and a determination image generation means that generates the first determination image based on the first image capturing result and generates the second determination image based on the second image capturing result, the first and second illumination means being arranged with the image capturing means interposed therebetween to illuminate the inspection surface with the first and second illumination light from mutually different directions.

According to the first to twenty-sixth aspects of the present invention, it is possible to more reliably determine the presence or absence of any crack on the inspection surface of the ceramic body than conventionally done, by a simple method involving image capturing using two illumination light having different illumination directions and comparison of two determination images generated based on a result of the image capturing.

In particular, according to the sixth, seventh, thirteenth, and fourteenth aspects, it is possible to reliably determine the presence or absence of any crack on the inspection surface of the ceramic body by automatic processing.

In particular, according to the seventh and fourteenth aspects, it is possible to reliably determine whether a deformation generated on the inspection surface of the ceramic body is a crack along a predetermined direction or an undulation. This allows reliable detection of any crack and avoids false detection of an undulation as a crack, thereby reducing over-detection.

In particular, according to the eighth to tenth aspects, the two determination images can be obtained as images at completely identical positions once image capturing of the entire inspection surface is performed through image capturing using two illumination light having different wavelength bands in addition to different illumination directions, and thus it is possible to more accurately determine the presence or absence of any crack by a simple method of comparison of the two determination images.

In particular, according to the tenth and fifteenth to nineteenth aspects, it is possible to more efficiently perform image capturing of the inspection surface of a ceramic body shaped in a tube and so on.

In particular, according to the seventeenth aspect, the two determination images can be obtained as images at completely identical positions only by rotating a ceramic body shaped in a cylinder, and thus it is possible to faster and more accurately determine the presence or absence of any crack.

In particular, according to the twentieth to twenty-second aspects, it is possible to check the presence or absence of any crack on the inspection surface of the ceramic body by a simple method involving comparison of the two determination images displayed on the image display means.

In particular, according to the twenty-fifth aspect, it is possible to reliably determine whether a deformation generated on the inspection surface of the ceramic body is a crack along an extrusion direction at extrusion shaping or an undulation. This allows reliable detection of any crack along the extrusion direction and avoids false detection of an undulation as a crack, thereby reducing over-detection.

BRIEF DESCRIPTION OF DRAWINGS

FIG. 9 is a block diagram of components provided to the surface inspecting apparatus 1 according to a modification.

DESCRIPTION OF EMBODIMENT

<Surface Inspecting Apparatus and Honeycomb Structural Body>

Figure 1A:
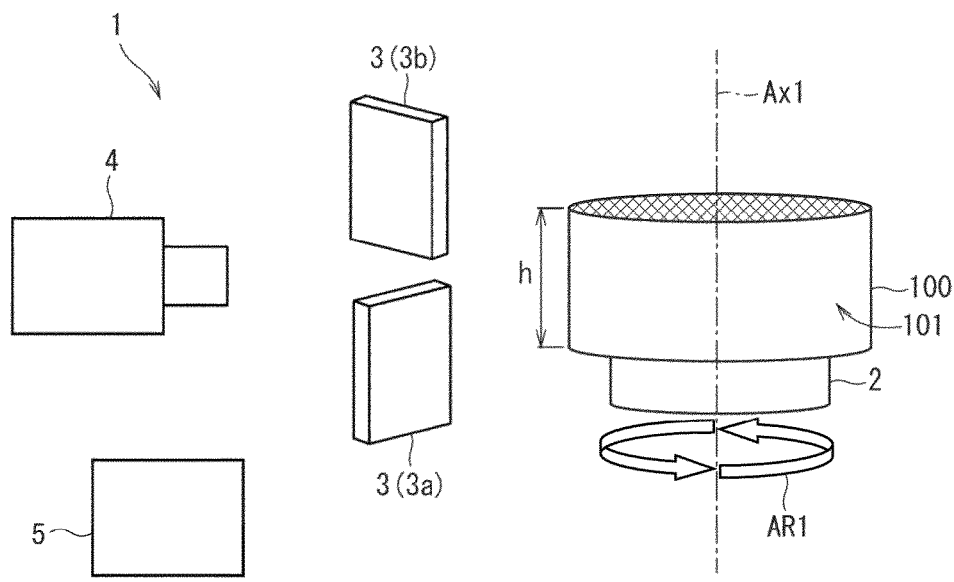
FIGS. 1A and 1B are diagrams illustrating a surface inspecting apparatus 1 together with a honeycomb structural body 100 as an inspection target thereof.
Figure 1B:
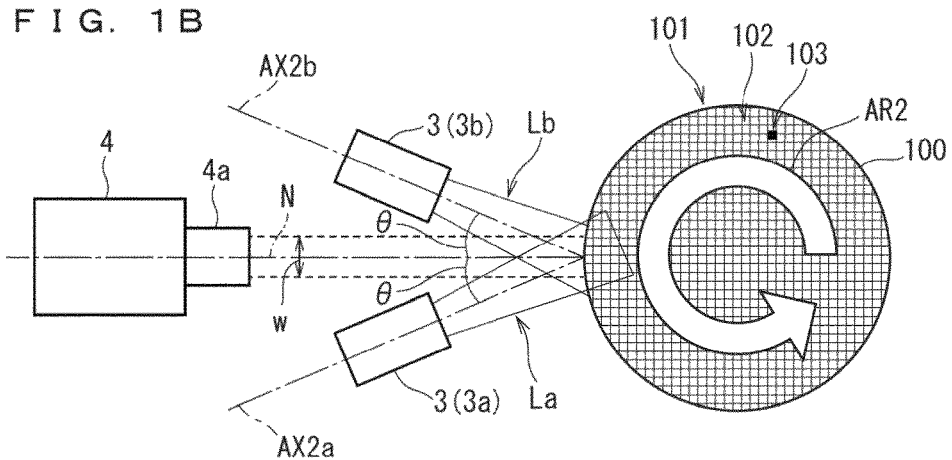
Figure 2:
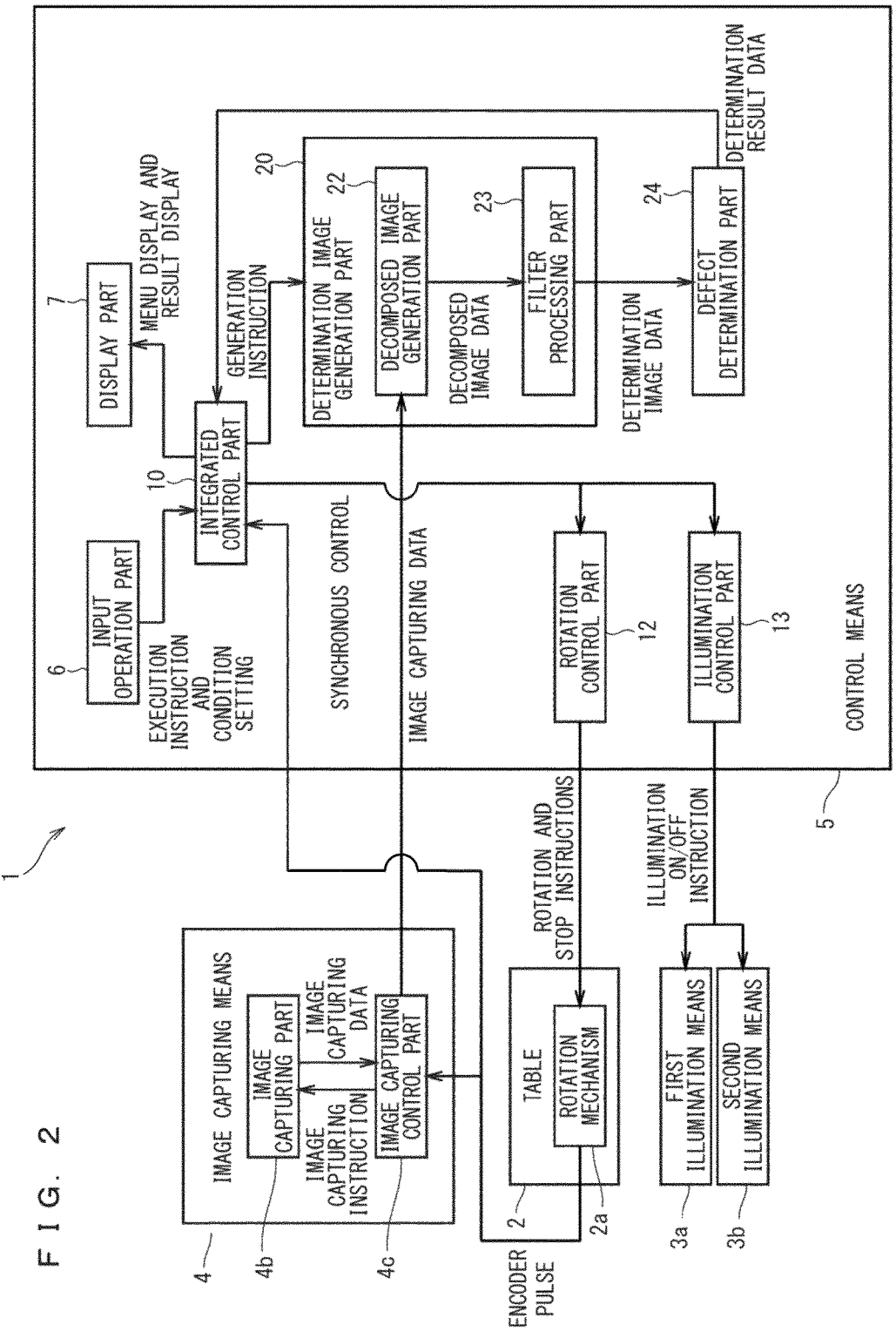
FIG. 2 is a block diagram of components provided to the surface inspecting apparatus 1.

FIGS. 1A and 1B are diagrams illustrating a surface inspecting apparatus 1 according to a preferred embodiment of the present invention together with a honeycomb structural body 100 as an inspection target thereof. FIG. 1A is a diagram schematically illustrating a spatial arrangement relation among components of the surface inspecting apparatus 1 and the honeycomb structural body 100. FIG. 1B is a planar arrangement diagram of a main part of the surface inspecting apparatus 1. FIG. 2 is a block diagram of components provided to the surface inspecting apparatus 1.

The surface inspecting apparatus 1 targets a surface (outer surface) of an outer wall 101, as a side surface, of the honeycomb structural body 100 having a cylindrical shape for an inspection surface, and inspects the presence or absence of any defect occurring on the outer wall 101. The surface inspecting apparatus 1 performs image capturing of the surface of the outer wall 101 parallel to the central axis AX1 under predetermined illumination light while rotating the honeycomb structural body 100 schematically about a central axis AX1 thereof, and determines the presence or absence of any defect on the outer wall 101 based on a result of the image capturing. The honeycomb structural body 100 is a cylindrical structural body whose both ends are open and which includes inside what is called a honeycomb structural body (honeycomb construction). The honeycomb structural body 100 includes, in an internal space surrounded by the outer wall 101 having a cylindrical shape, a plurality of cells 103 partitioned by a partition 102 and each aligned with a direction (axial direction) of the central axis AX1 of the honeycomb structural body 100. In FIG. 1B, only one of the cells 103 is colored to help understanding, but in reality, all of the cells 103 penetrate in the axial direction.

For example, the thickness of the outer wall 101 is 500 μm to 1 mm approximately, the thickness of the partition 102 is 50 μm to 300 μm approximately, and the pitch of the partition 102 that defines the sizes of the cells 103 is 0.5 mm to 2.0 mm approximately. The length (height h) of the axial direction is 40 mm to 400 mm approximately, and the radius (sectional radius) of a section vertical to the axial direction is 20 mm to 200 mm approximately.

In the present preferred embodiment, an aspect in which the honeycomb structural body 100 includes the cells 103 having square sections and uniform sizes is described but is exemplary, and the cells 103 may have a regular hexagonal section or a circular section, or may include cells 103 having different sizes.

The honeycomb structural body 100 according to the present preferred embodiment is a fired body of ceramic (for example, alumina), and is manufactured by shaping, by an extrusion molding method, a clay body obtained by mixing ceramic powder as a component material of the fired body with organic binder, water and the like to obtain a honeycomb compact, and then firing the honeycomb compact (ceramics compact) thus obtained.

A crack and adhesion of a foreign substance are exemplified as defects occurring on the outer wall 101 of the honeycomb structural body 100, but a detection target of the surface inspecting apparatus 1 according to the present preferred embodiment is, among these defects, at least a crack occurring on the outer wall 101 along the axial direction of the honeycomb structural body 100. In the present preferred embodiment, a crack occurring in this manner is also referred to as an axial direction crack. Although described later in detail, the axial direction crack includes, in addition to a typical crack CR (refer to FIG. 3) that provides a gap in the outer wall 101, a step (step crack) ST (refer to FIG. 3) occurring when part of the outer wall 101 along the axial direction shifts in a radial direction.

As illustrated in FIG. 1A, the surface inspecting apparatus 1 mainly includes a table 2 on which the honeycomb structural body 100 is mounted at inspection, a pair of illumination means 3 (first illumination means 3a and second illumination means 3b) that illuminate the honeycomb structural body 100 mounted on the table 2 with illumination light, image capturing means 4 that generates image data (image capturing data) by performing image capturing of the surface of the outer wall 101 of the honeycomb structural body 100, and control means 5 controlling the entire operation of the surface inspecting apparatus 1 and also configuring various kinds of processing part to perform image processing based on the image capturing data obtained by the image capturing means 4, and determine the presence or absence of any defect based on a result of the processing.

The table 2 has a mounting surface on which the honeycomb structural body 100 can be mounted in a posture that the central axis AX1 thereof substantially matches with a vertical direction. The table 2 also comprises a rotation mechanism 2a (refer to FIG. 2) not illustrated in FIGS. 1A and 1B. Owing to comprising the rotation mechanism 2a, the table 2 is rotatable in a horizontal plane as illustrated with arrows AR1 and AR2 in FIGS. 1A and 1B. For example, a turntable is used as the rotation mechanism 2a. The table 2 is a component that functions as a holding part that holds the honeycomb structural body 100 rotatable about the central axis AX1 thereof.

The rotation mechanism 2a includes an encoder (not illustrated), and a pulse (encoder pulse) is provided to the image capturing means 4 (more specifically, an image capturing control part 4c) from the encoder each time the table 2 rotates by a constant angle.

The honeycomb structural body 100 is mounted on the mounting surface of the table 2 so that the central axis AX1 thereof matches with a rotation center of the table 2. A table having a plane size smaller than the size of a section vertical to the central axis AX1 of the honeycomb structural body 100 is used as the table 2. This is to avoid capturing of an image of the table 2 at image capturing by the image capturing means 4.

As illustrated in FIG. 1B, the first illumination means 3a and the second illumination means 3b as a pair of the illumination means 3 are arranged at positions symmetric with respect to the direction of a normal N of the outer wall 101 of the honeycomb structural body 100 mounted on the table 2 in plan view. The first illumination means 3a and the second illumination means 3b are arranged so that illumination light (first illumination light) La of the former and illumination light (second illumination light) Lb of the latter are incident on an identical position on the outer wall 101, in other words, an overlapping range exists in an illuminated region of each of the first illumination means 3a and the second illumination means 3b, and so that illumination angles (angles between an optical axis centers AX2a and AX2b of each illumination light and the normal N of the outer wall 101) of the first illumination means 3a and the second illumination means 3b are an identical angle θ in plan view. With satisfying this arrangement relation, the first illumination means 3a and the second illumination means 3b are arranged with the image capturing means 4 interposed therebetween and capable of irradiating the side surface of the honeycomb structural body 100 as an inspection surface with the first illumination light La and the second illumination light Lb in mutually different directions. The angle θ is a value in a range of 5°≤θ≤30°. Hereinafter, unless otherwise mentioned, the overlapping region between the illuminated regions with the first illumination light La and the second illumination light Lb is simply referred to as an illuminated region.

However, illumination means that emit illumination light having wavelength bands different from each other (not overlapping) are used as the first illumination means 3a and the second illumination means 3b. The first illumination light La and the second illumination light Lb having different wavelength bands are illuminated to the illuminated region in a superimposed manner.

For example, it is a preferable manner that the first illumination means 3a is provided to emit red light as the first illumination light La, and the second illumination means 3b is provided to emit blue light as the second illumination light Lb. Alternatively, in another manner, the first illumination means 3a may be provided to emit white light as the first illumination light La, and the second illumination means 3b may be provided to emit ultraviolet light as the second illumination light Lb. In this preferred embodiment, red light is defined as light belonging to a wavelength band with an emission wavelength of 600 nm to 800 nm, and blue light is defined as light belonging to a wavelength band with an emission wavelength of 400 nm to 500 nm. In addition, white light is defined as light belonging to a wavelength band with an emission wavelength of 300 nm to 800 nm, and ultraviolet light is defined as light belonging to a wavelength band with an emission wavelength of 100 nm to 400 nm.

In a preferable example, an LED that emits single-color light satisfying an above-described wavelength band is used as an illumination light source provided to the illumination means 3. However, as another manner, light emitted from, for example, an LED, a metal halide lamp, or any other light source that emit white light may be transmitted through a color filter that transmits only light satisfying any above-described wavelength band, and then made incident on the honeycomb structural body 100.

In the case that an LED is used as the illumination light source, it is preferable that the illumination means 3 further includes a light condensing lens (not illustrated) that condenses light emitted from the LED, and light through the light condensing lens is made incident on the honeycomb structural body 100, in terms of achieving an increased illumination intensity of the illumination light.

In the image capturing means 4, at least a light-receiving part 4a thereof is arranged on the normal N of the outer wall 101 of the honeycomb structural body 100, which is also the axis of symmetry of the arrangement positions of the first illumination means 3a and the second illumination means 3b, and the image capturing means is capable of capturing, in the range of an image capturing width w, an image of the illumination light emitted from the illumination means 3 on the normal N of the illumination region, at the arrangement position of the image capturing means 4.

Although not illustrated in FIGS. 1A and 1B, the image capturing means 4 includes an image capturing part 4b and the image capturing control part 4c in addition to the light-receiving part 4a as illustrated in FIG. 2. The image capturing part 4b is a component which performs an actual image capturing operation (image capturing based on an image capturing instruction) in the image capturing means 4. The image capturing control part 4c is a component that performs the image capturing instruction to the image capturing part 4b, acquisition of image capturing data from the image capturing part 4b, and processing of combining the acquired image data from each image capturing width w to generate continuous image data as one piece of captured image data on the entire surface of the outer wall 101.

In the surface inspecting apparatus 1 according to this preferred embodiment, image capturing of the surface of the outer wall 101 of the honeycomb structural body 100 rotated in the horizontal plane by the table 2 is repeatedly performed using the image capturing means 4 at each predetermined image capturing width w under the illumination light emitted from the pair of the illumination means 3, and finally, a captured image of the entire outer wall 101 is obtained. This is achieved by repeatedly performing the image capturing at the image capturing part 4b at a constant timing (time interval) while the table 2 is rotated at a predetermined rotational speed (angular velocity). A plurality of captured images each obtained for the image capturing width w are provided with image processing by various kinds of processing parts comprised in the surface inspecting apparatus 1 as described later, and are used in determination of the presence or absence of any defect (in particular, crack) on the outer wall 101 of the honeycomb structural body 100.

The image capturing width w and the distance (imaging distance) between the image capturing means 4 and the honeycomb structural body 100 may be determined as appropriate in accordance with the sectional radius of the honeycomb structural body 100. in other words, when the image capturing width w is too large as compared to the sectional radius, the ratio of a range in an in-focus state relative to the image capturing width w in a captured image is small, which is not preferable. In addition, when the image capturing width w is too small or when the imaging distance is too large, the resolution of a captured image degrades, which is not preferable. When the sectional radius is 20 mm to 250 mm approximately as described above, the image capturing width w is preferably 10 μm to 3 cm approximately, and the imaging distance is preferably 30 cm to 200 cm approximately.

More specifically, the image capturing means 4 (image capturing part 4b) has a favorable sensitivity to the wavelength bands of the first illumination light La emitted by the first illumination means 3a and the second illumination light Lb emitted by the second illumination means 3b, and is capable of generating an image formation signal for a color component corresponding to a predetermined wavelength range and passing the image formation signal from the image capturing control part 4c to the control means 5. The image formation signal is a signal indicating the coordinate position in a captured image and a signal amount at the coordinate position. This is achieved by, for example, the image capturing means 4 generating the image capturing data in a data format in which a pixel value (color concentration value at each pixel position) for each color component is independently (individually) described. In this case, the pixel position of each pixel corresponds to a coordinate position in the image formation signal, the pixel value corresponds to the signal amount at the coordinate position. Hereinafter, unless otherwise mentioned, description will be made on a case in which the image capturing means 4 generates the image capturing data in the data format in which a pixel value for each color component is independently described in this manner.

A line sensor individually having light-receiving sensitivities for respective light of different color components (wavelength ranges) and capable of outputting the image capturing data in which a pixel value for each color component is independently described is exemplarily described as the image capturing means 4. For example, when the first illumination light La is red light and the second illumination light Lb is blue light as described above, a well-known RGB line sensor can be used as the image capturing means 4. The RGB line sensor is capable of receiving green light in addition to red light and blue light and outputting data in an RGB format as the image capturing data, but information related to the light intensity value (pixel value) of green light is not used in the present preferred embodiment. When the line sensor is used as the image capturing means 4, the light-receiving part 4a is preferably arranged such that a longitudinal direction thereof is parallel to the axial direction of the honeycomb structural body 100.

However, it is not essential that the line sensor is used as the image capturing means 4, and an area camera having a two-dimensional (rectangular) image capturing range, such as a digital camera, may be used.

Image capturing means that has individual light-receiving sensitivities to light of different color components (wavelength ranges) and outputs the image capturing data in a format in which information on pixel values for color components is synthesized for each pixel position may be used as the image capturing means 4. However, in this case, it is required that the pixel value information of each color component can be restored at processing at a later stage as appropriate.

Preferably, the image capturing means 4 is provided such that image capturing with the image capturing width w is possible over the entire range (range of the height h illustrated in FIG. 1A) of the honeycomb structural body 100 in the axial direction. This can be achieved by using, for example, a line sensor capable of performing image capturing in such an image capturing range as the image capturing means 4. In this case, the illumination means 3 is provided such that the illumination light is incident over at least the entire image capturing range at an illumination intensity suitable for image capturing by the image capturing means 4. When the illumination means 3 and the image capturing means 4 satisfy these requirements, it is possible to perform image capturing of the entire surface of the outer wall 101 while the honeycomb structural body 100 is rotated once.

However, this aspect is not essential, and the image capturing means 4 may be provided movable in the vertical direction relative to the honeycomb structural body 100 mounted on the table 2 and perform image capturing at each part obtained by dividing the range of the height h. The surface inspecting apparatus 1 may include a plurality of the image capturing means 4 in the vertical direction, and the range of the height h may be captured as a whole through image capturing of different ranges by the respective image capturing means 4.

The control means 5 is achieved by, for example, a computer (not illustrated) including a CPU, a ROM, a RAM, and a storage medium including a HDD. In the surface inspecting apparatus 1, operation and processing of each component are achieved through execution, by the CPU, of an operation program stored in the storage medium in advance. The arrangement position of the control means 5 is not particularly limited as long as electrical connection is established with each of the rotation mechanism 2a of the table 2, the pair of the illumination means 3, and the image capturing means 4 described above.

As illustrated in FIG. 2, the control means 5 comprises an input operation part 6 that is a keyboard, a touch panel or the like and allows various kinds of input operations such as an inspection execution instruction and condition setting externally provided to the surface inspecting apparatus 1, and a display part 7 that is, for example, a liquid crystal display for performing display of an operation menu and an inspection result.

In addition, the control means 5 mainly includes an integrated control part 10, a rotation control part 12, an illumination control part 13, a determination image generation part 20, and a defect determination part 24, as functional components implemented through execution of the operation program by the CPU.

The integrated control part 10 is a component that integrally controls operation of each component of the surface inspecting apparatus 1. In other words, each component of the surface inspecting apparatus 1 performs operation thereof based on a control signal from the integrated control part 10.

The rotation control part 12 is a component that controls operation (rotation of the table 2 and stop thereof) of the rotation mechanism 2a provided to the table 2. In other words, in the surface inspecting apparatus 1, rotation operation of the table 2 and stop thereof are achieved through a rotation instruction signal and a stop instruction signal that are provided to the rotation mechanism 2a from the rotation control part 12 based on the control signal from the integrated control part 10.

The illumination control part 13 is a component that controls operation of the first illumination means 3a and the second illumination means 3b. In other words, in the surface inspecting apparatus 1, illumination with the illumination light from the first illumination means 3a and the second illumination means 3b and stop thereof are achieved by an on/off instruction signal (turning on/off instruction signal) for the illumination light provided to the first illumination means 3a and the second illumination means 3b from the illumination control part 13 based on the control signal from the integrated control part 10.

The determination image generation part 20 is a component that performs, based on image data of the outer wall 101 of the honeycomb structural body 100 obtained by the image capturing means 4, processing of generating image data (determination image data) representing an image (determination image) used to determine any crack on the outer wall 101. The determination image generation part 20 mainly includes a decomposed image generation part 22 and a filter processing part 23.

The decomposed image generation part 22 is a component that acquires the image capturing data generated by the image capturing means 4 and generates first decomposed image data and second decomposed image data from the image capturing data. Although the first decomposed image data is mainly intended to be generated as image data of an image formed through illumination with the first illumination light La, and the second decomposed image data is mainly intended to be generated as image data of an image formed through illumination with the second illumination light Lb, it is allowed that an image formed by other light such as external light is included in each piece of image data to such an extent that no disadvantage is caused to determination of the presence or absence of any crack through comparison of two determination images performed at the defect determination part 24 in a manner to be described later.

The filter processing part 23 is a component that performs filter processing, as appropriate, on two pieces of image data generated by the decomposed image generation part 22 so that they represent images preferable for defect determination performed at the defect determination part 24. Binarization processing, shading correction, and contraction-expansion processing are exemplarily listed as this filter processing. Two pieces of decomposed image data after the filter processing are provided from the determination image generation part 20 to the defect determination part 24 as determination image data at determination of the presence or absence of any crack.

The defect determination part 24 is a component that performs determination processing of determining any defect on the outer wall 101. The defect determination part 24 performs at least determination processing of comparing two determination images (more specifically, comparing two pieces of determination image data), and determining the presence or absence of any crack in the axial direction occurring on the outer wall 101 based on a difference in between formation manners of shadow regions in the two determination images. Preferably, the defect determination part 24 also performs, when it is determined that the axial direction crack exists, specification of the kind (typical crack CR or step ST) of the axial direction crack being a determination target and specification of a position at which the axial direction crack occurs as part of the determination processing. This determination processing will be described later in detail.

However, the presence or absence of any crack occurring in any other manner (for example, occurring in a direction other than the axial direction), adhesion of a foreign substance, or the like may be determined at the defect determination part 24 in an appropriate processing manner. The control means 5 may include any other functional component (not illustrated) necessary for this.

<Deformation Type of Outer Wall>

Figure 3:
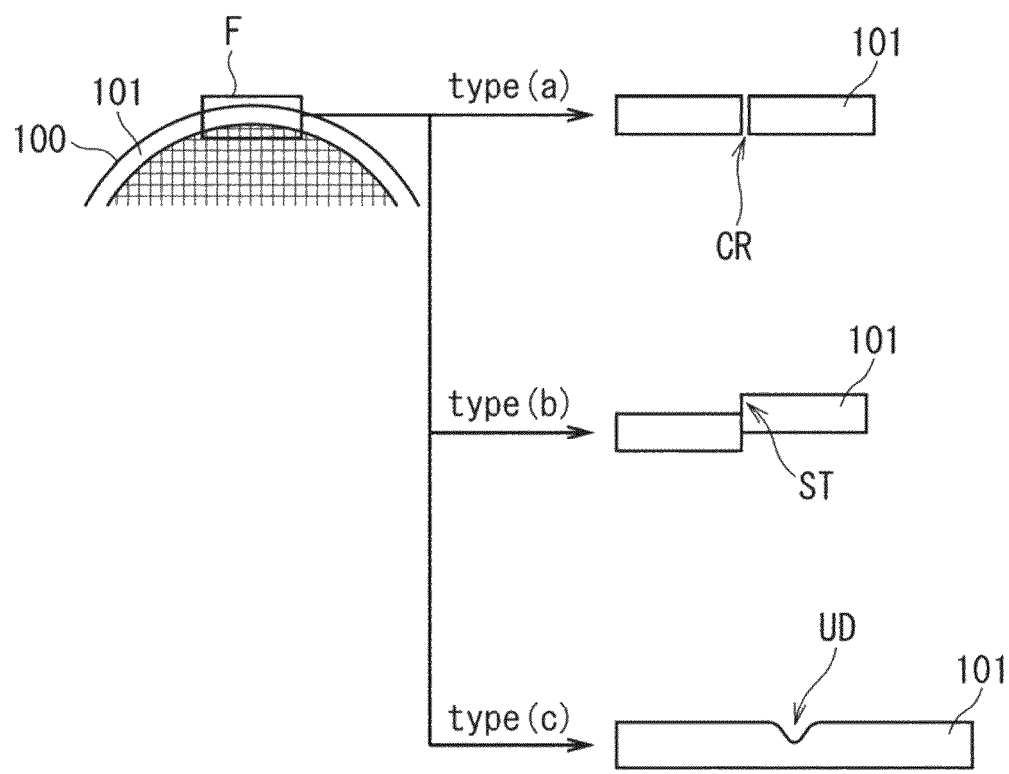
FIG. 3 is a diagram illustrating the type of a deformation occurring on an outer wall 101 of the honeycomb structural body 100 along an axial direction thereof, with an enlarged view of part F of a section vertical to the axial direction.

Subsequently, before description of the determination processing for the presence or absence of any crack in the axial direction, the type of a deformation occurring in the axial direction on the outer wall 101 of the honeycomb structural body 100, which is an assumption for this determination processing, will be described. FIG. 3 is a diagram illustrating the type of deformation occurring on the outer wall 101 of the honeycomb structural body 100 along the axial direction thereof, with an enlarged view of part F of a section vertical to the axial direction.

It is desired that the honeycomb structural body 100 is ideally manufactured such that the outer wall 101 thereof is uniformly smooth with no defect, however in reality, because of a method of the manufacturing, more specifically, because of manufacturing through shaping by the extrusion molding method and the following process of firing, deformation may occur in the axial direction of the honeycomb structural body 100 as an extrusion direction at the extrusion shaping. Specifically, a failure occurring to a honeycomb compact along the axial direction thereof due to, for example, moisture deficiency when the compact is obtained by the extrusion shaping, and alternatively, contraction occurring to the honeycomb structural body 100 when the temperature is decreased after the honeycomb compact is formed into the honeycomb structural body 100 by firing, are exemplified as factors of the deformation.

Specific deformation types include three types illustrated as type (a), type (b), and type (c) in FIG. 3.

First, type (a) is the typical crack CR occurring in a manner that a gap is generated on the outer wall 101 along the axial direction. The crack CR is formed through the outer wall 101 as illustrated in FIG. 3 in most cases, but a gap not penetrating through the outer wall 101 and closed on an inner surface side is also included in type (a). Most of axial direction cracks occurring in the honeycomb structural body 100 are the crack CR of type (a). In FIG. 3, two opposing end faces of the outer wall 101 forming the crack CR are both illustrated flatly, but in reality, there are some cases that the end faces are formed in a manner that the end faces include minute unevenness reflecting the shapes of ceramic crystal grains. Most of axial direction cracks are formed as the crack CR. The width of the crack CR in a circumferential direction is 20 μm to 500 μm approximately. Since the depth of the crack CR is equal to the thickness of the outer wall 101 when the crack CR penetrates through, an upper limit of the depth is this thickness, and a lower limit when the crack CR does not penetrate through is approximately 50 μm or larger.

Subsequently, type (b) is the step (step crack) ST occurring as a result that a part of the outer wall 101 along the axial direction is displaced in the radial direction. In FIG. 3, a case in which the right side is relatively higher and the left side is relatively lower is exemplarily illustrated, but it is clear that the step ST can occur in the opposite manner. The step ST is unlikely to occur as compared to the crack CR, but is same as the crack CR in that the step ST causes discontinuity on the outer wall 101, and in this preferred embodiment, similarly to the crack CR, the step ST is treated as the axial direction crack to be detected. The height of the step ST is 50 μm to 1 mm approximately.

Type (c) is an undulation UD as a relief occurring along the circumferential direction on the surface of the outer wall 101. More specifically, in FIG. 3, a concave portion having a longitudinal direction along the axial direction of the honeycomb structural body caused by the occurrence of the undulation UD is exemplarily illustrated. The undulation UD can be formed as a protruding portion, but the following description is targeted on the undulation UD forming a concave portion in a manner aligned with the axial direction, in order to facilitate comparison with the crack CR described above.

The width of the undulation UD in the circumferential direction is 200 μm to 1 mm approximately. The depth of the undulation UD is also 200 μm to 1 mm approximately.

In the honeycomb structural body 100, the three types of deformation as described above occur. Among these, the crack CR and the step ST collectively referred to as the axial direction crack are to be reliably detected by the surface inspecting apparatus 1 according to the present preferred embodiment. The undulation UD does not affect the quality and characteristic of the honeycomb structural body, and thus the existence thereof is allowed. In other words, the surface inspecting apparatus 1 is required to reliably detect the axial direction crack at defect determination, but not to perform over-detection that the undulation UD is detected as the axial direction crack.

<Inspection Process>

A typical processing process for inspecting the presence or absence of any crack in the axial direction, which is performed at the surface inspecting apparatus 1 having the above-described configuration, will be described next. Hereinafter, for simplification of description, unless otherwise mentioned, it is supposed that the first illumination means 3a emits red light as the first illumination light La, the second illumination means 3b emits blue light as the second illumination light Lb, the image capturing means 4 is an RGB line sensor that generates the image capturing data in the RGB format, and the illumination means 3 and the image capturing means 4 are provided to be capable of executing image capturing on the entirety of the surface of the outer wall 101, as the side surface, of the honeycomb structural body 100 while the honeycomb structural body 100 rotates once.

First, the honeycomb structural body 100 as an inspection target is mounted and fixed on the table 2. The mounting of the honeycomb structural body 100 on the table 2 may be manually performed by a worker, or may be automatically performed by a predetermined convey means provided outside of the apparatus.

After this mounting is performed, an inspection start instruction is provided to the integrated control part 10 through the input operation part 6. Parameters necessary for inspection, such as the size of the honeycomb structural body 100, the rotational speed of the table 2, the intensity of illumination light, an image capturing condition including an image capturing timing (time interval) and the like, a filter processing condition, and a condition of the determination processing of the axial direction crack are set in advance through the input operation part 6. In another aspect, the mounting and fixation of the honeycomb structural body 100 may be automatically detected and the inspection start instruction may be automatically provided to the integrated control part 10.

Having received the inspection start instruction, the integrated control part 10 controls the rotation control part 12 and the illumination control part 13 in a synchronized manner.

Specifically, the integrated control part 10 first instructs the rotation control part 12 to rotate the rotation mechanism 2a provided to the table 2 on which the honeycomb structural body 100 is mounted, and instructs the illumination control part 13 to perform illumination with illumination light by the first illumination means 3a and the second illumination means 3b. When the rotation control part 12 and the illumination control part 13 each issue a drive signal in accordance with an instruction signal provided from the integrated control part 10, the table 2 on which the honeycomb structural body 100 is mounted rotates at a rotational speed set in advance, and the first illumination light La and the second illumination light Lb having intensities set in advance are emitted from the first illumination means 3a and the second illumination means 3b to the rotating honeycomb structural body 100 in a superimposed manner (simultaneously) as illustrated in FIG. 1B.

After a rotation operation of the table 2 is started, an encoder (not illustrated) provided to the rotation mechanism 2a issues a pulse (encoder pulse) at a predetermined time interval. This encoder pulse is passed to the image capturing control part 4c of the image capturing means 4. The image capturing control part 4c provides an image capturing instruction to the image capturing part 4b to execute image capturing in synchronization with a timing at which this encoder pulse is received. As a result that the image capturing is performed at a timing when the encoder pulse is issued in this manner, image capturing data is generated at the image capturing means 4 as data set of a pixel value for each RGB color component at individual image capturing and the pulse value of the encoder pulse at image capturing.

Since the image capturing means 4 performs image capturing with the image capturing width w as described above, if at least $2\pi r/w$ times of image capturing is performed in a time of $4\pi/\omega$ (sec) in which the honeycomb structural body 100 rotates once, that is, image capturing is performed once in each time of $2w/r\omega$ (sec) where the sectional radius of the honeycomb structural body 100 is represented by r and the rotational angular speed of the table 2 (honeycomb structural body 100) is represented by $\omega$ (rad/sec), image capturing can be performed on the entire surface of the outer wall 101 while the honeycomb structural body 100 rotates once, but in reality, it is preferable that sequentially captured images have an overlapping with 50% approximately or lower, and thus the time interval of image capturing is preferably set to be smaller than $2w/r\omega$ (sec).

For example, when the honeycomb structural body 100 with r=5.0 cm is rotated at $\omega=230°/sec$ and image capturing is performed by the image capturing means 4 (line sensor) with w=30 m, the time interval of the image capturing is set to be $1.0\times10^{-4}$ sec to $1.4\times10^{-4}$ sec approximately. In this case, the number of times of image capturing is 10500 to 15000 approximately. In other words, image capturing data of 10500 lines to 15000 lines approximately is acquired at inspection of the single honeycomb structural body 100.

The image capturing data obtained by the image capturing means 4 is provided to the decomposed image generation part 22 of the determination image generation part 20 sequentially or all at once by each a predetermined data amount (for example, at each completion of image capturing of the single honeycomb structural body 100).

Judgement of completion of the image capturing of the entire surface of the outer wall 101 at each honeycomb structural body 100 is performed by the integrated control part 10. Specifically, at the integrated control part 10, a time taken for image capturing of the entire surface of the outer wall 101 is calculated from, for example, the size of the honeycomb structural body 100 and the rotational speed of the table 2 input through the input operation part 6 in advance before the inspection, and a timing at which the image capturing is started can be known through acquisition of the encoder pulse issued by the rotation mechanism 2a together with the image capturing means 4. A timing at which the image capturing of the entire surface of the outer wall 101 is completed can be judged from the timing at which the image capturing starts and the time taken for the image capturing.

Alternatively, image capturing of the outer wall 101 of the honeycomb structural body 100 can be performed at a constant interval by performing acquisition of the image capturing data for a constant number of times of image capturing (the number of acquired lines) at each inputting of a constant number of encoder pulses in accordance with the rotation angle of the table 2 to the integrated control part 10, and by automatically ending image capturing based on, for example, the rotation angle of the table 2 set in advance, the number of acquired lines, and the number of encoder pulses.

A large number of pieces of the image capturing data acquired between timings at which image capturing starts and ends and arranged according to a temporal sequence represent a single piece of the image capturing data of the entire surface of the outer wall 101. In the present preferred embodiment, this single image capturing data is referred to as continuous image data.

At a timing when the image capturing of the entire surface of the outer wall 101 is completed, the integrated control part 10 instructs the decomposed image generation part 22 to generate decomposed image data based on the continuous image data. The integrated control part 10 also provides the rotation control part 12 with an instruction signal to stop the rotation of the rotation mechanism 2a, and provides the illumination control part 13 with an instruction signal to end illumination with the first illumination light La and the second illumination light Lb. When the rotation control part 12 and the illumination control part 13 issue drive signals in response to these instruction signals, the rotation of the table 2 is stopped, and the first illumination light La and the second illumination light Lb are turned off. The first illumination light La and the second illumination light Lb may be always turned on. When the rotation of the table 2 is completely stopped, the honeycomb structural body 100, image capturing of which has ended, is moved from the table 2, and instead, the honeycomb structural body 100, image capturing of which is subsequently performed, is mounted on the table 2.

The decomposed image generation part 22 generates the first decomposed image data and the second decomposed image data from the continuous image data generated as a single piece of RGB image data. Since it is supposed that the first illumination light La is red light and the second illumination light Lb is blue light, it is a preferable example that the first decomposed image data is generated as image data (R image data) that is only an R component extracted from the continuous image data, and the second decomposed image data is generated as image data (B image data) that is only a B component extracted from the continuous image data. For example, when a pixel value (color concentration value) at an optional pixel (x, y) of the continuous image data is expressed as $(R_{xy}, G_{xy}, B_{xy})$, the decomposed image generation part 22 preferably generates the first decomposed image data and the second decomposed image data, respectively, R image data the pixel value of which at the pixel (x, y) is expressed as $(R_{xy}, 0, 0)$ and B image data the pixel value of which at the pixel (x, y) is expressed as $(0, 0, B_{xy})$.

The R image data and the B image data in this case substantially correspond to image capturing data obtained by performing image capturing by the image capturing means 4 at illumination only with the first illumination light La, and image capturing data obtained by performing image capturing by the image capturing means 4 at illumination only with the second illumination light Lb, respectively.

However, as described above, as long as no disadvantage is caused to determination at the defect determination part 24, for example, as long as the pixel value is smaller than a predetermined threshold, the first decomposed image data may include any color component other than the R component and the second decomposed image data may include any color component other than the B component. In other words, as in the above-described example, when the pixel value (color concentration value) of the continuous image data at the optional pixel (x, y) is expressed as $(R_{xy}, G_{xy}, B_{xy})$, the pixel value of the first decomposed image data at the pixel (x, y) may be expressed as $(R_{xy}, g1_{xy}, b1_{xy})$, and the pixel value of the second decomposed image data at the pixel (x, y) may be expressed as $(r2_{xy}, g2_{xy}, B_{xy})$. In the following, pixel values smaller than the predetermined threshold are expressed as $g1_{xy}$, $b1_{xy}$, $r2_{xy}$, and $g2_{xy}$.

In the case that any image capturing means that has individual light-receiving sensitivities to light of different color components (wavelength ranges) as described above and outputs image capturing data in the format in which information on pixel values for color components is synthesized for each pixel position is used as the image capturing means 4, the decomposed image generation part 22 generates the first decomposed image data and the second decomposed image data by restoring pixel value information of each color component from the image capturing data.

The first decomposed image data and the second decomposed image data generated by the decomposed image generation part 22 are provided to the filter processing by the filter processing part 23. The filter processing part 23 performs the above-described binarization processing, the shading correction, the contraction-expansion processing, and the like on each of the first decomposed image data and the second decomposed image data.

Then, the first decomposed image data and the second decomposed image data provided with the filter processing by the filter processing part 23 are passed to the defect determination part 24 as first determination image data and second determination image data, respectively, and are used in determination of the presence or absence of any crack in the axial direction at the defect determination part 24. The determination processing at the defect determination part 24 will be described later in detail.

Determination result data in which a result of the determination obtained by the defect determination part 24 is described is passed to the integrated control part 10, and furthermore, is used for display of a determination result by the display part 7, and so on.

After the determination result is obtained, an inspection targeted to another honeycomb structural body 100 is subsequently performed in the same manner.

<Determination of Axial Direction Crack>

The determination at the defect determination part 24 is performed based on differences of the presence or absence of any shadow regions and formation positions thereof appearing in the images (a first determination image and a second determination image) schematically represented by the first determination image data and the second determination image data, respectively, at comparison of those images, the shadow regions being formed due to a deformation occurring to the surface of the outer wall 101.

Firstly, no shadow region is formed in the first determination image and the second determination image where no deformation occurs.

Figure 4A:
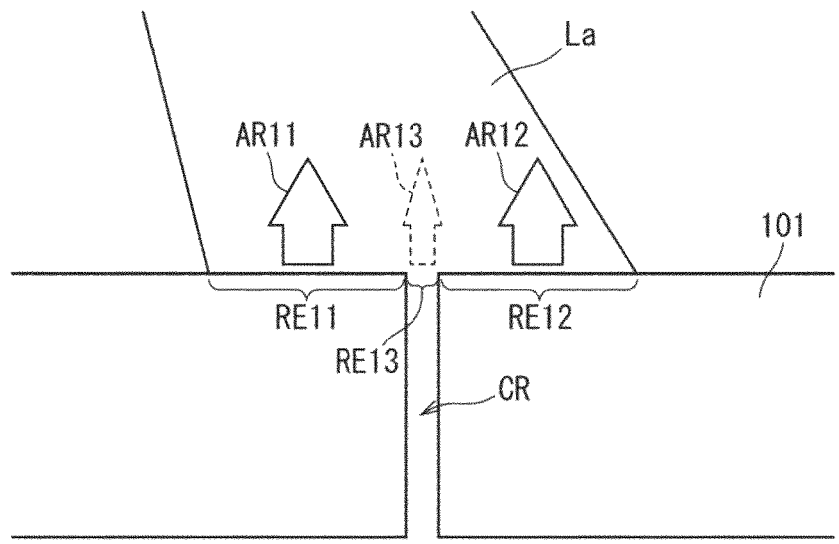
FIGS. 4A and 4B are diagrams for illustration of how an image is formed for a place where a crack CR is formed on the outer wall 101.
Figure 4B:
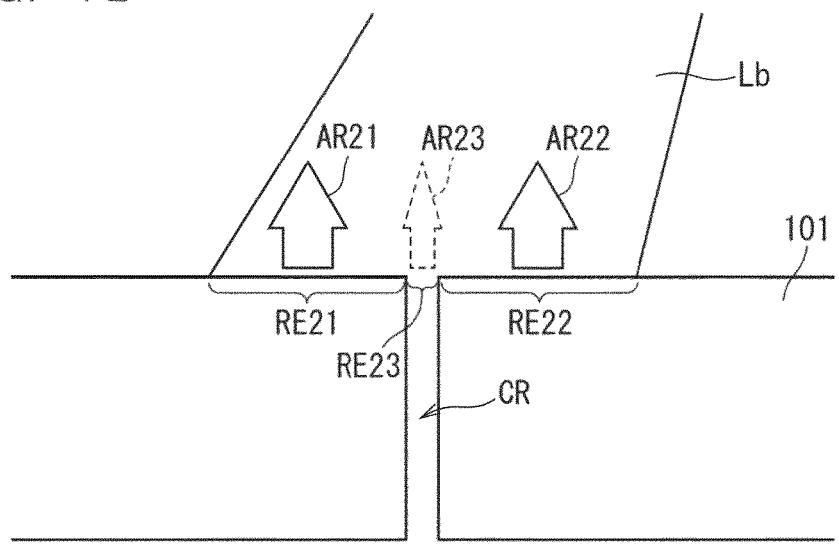

Next, a case in which the crack CR illustrated as type (a) in FIG. 3 is generated as a deformation will be described. FIGS. 4A and 4B are diagrams for illustration of how an image is formed for a place where the crack CR is formed on the outer wall 101.

FIG. 4A illustrates how an image is formed by the first illumination light La for a place where the crack CR is formed. As for regions RE11 and RE12 where no crack CR is formed, when the first illumination light La is incident on the surface of the outer wall 101 at the predetermined angle θ as described above, an image of the surface by the first illumination light La is formed at the image capturing means 4 (not illustrated) disposed at an upper position in FIG. 4A. In FIG. 4A, arrow AR11 and arrow AR12 illustrated with solid lines indicate that this image formation is performed (same in FIGS. 6 and 8).

On the other hand, a region RE13 where the crack CR is formed does not contribute image formation by the first illumination light La at the image capturing means 4. In other words, the image capturing means 4 does not obtain an image of the region RE13, and a shadow region is substituted for this region. In FIG. 4A, arrow AR13 illustrated with a broken line indicates that formation of this shadow region is performed (same in FIGS. 6 and 8).

Meanwhile, FIG. 4B illustrates how an image is formed with the second illumination light Lb at the place (place same as that in FIG. 4A) where the crack CR is formed. As for regions RE21 and RE22 (identical to the regions RE11 and RE12, respectively, in FIG. 4A) where no crack CR is formed, when the second illumination light Lb is incident on the surface of the outer wall 101 at the predetermined angle θ as described above, an image of the surface by the second illumination light Lb is formed at the image capturing means 4 as illustrated with arrow AR21 and arrow AR22.

On the other hand, a region RE23 (identical to the region RE13 in FIG. 4A) where the crack CR is formed does not contribute image formation by the second illumination light Lb at the image capturing means 4. In other words, the image capturing means 4 does not obtain an image of the region RE23, and a shadow region is substituted for this region as illustrated with arrow AR23.

Figure 5A:
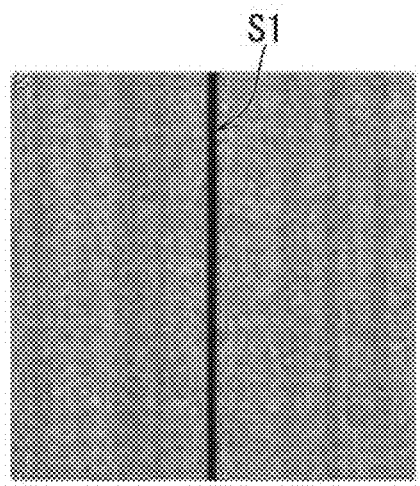
FIGS. 5A, 5B, and 5C are diagrams illustrating images of a place where the crack CR is formed on the actual outer wall 101.
Figure 5B:
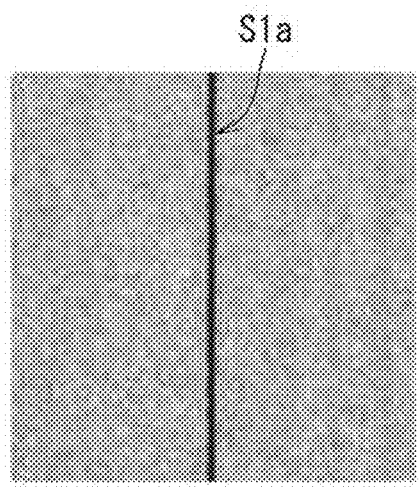
Figure 5C:
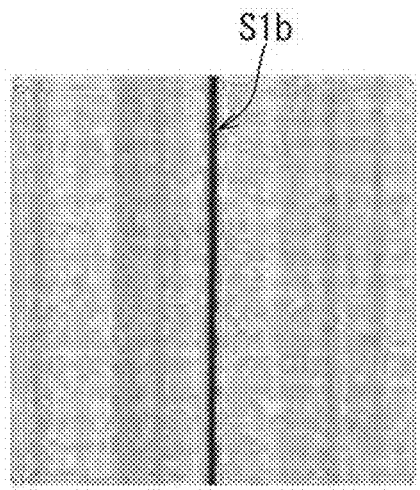

FIGS. 5A, 5B, and 5C are diagrams illustrating images of a place where the crack CR is formed on the actual outer wall 101. FIG. 5A is a captured image represented by image capturing data obtained by the image capturing means 4, FIG. 5B is the first determination image represented by the first determination image data generated by the determination image generation part 20 based on the image capturing data that provides the captured image of FIG. 5A, and FIG. 5C is the second determination image represented by the second determination image data generated in a similar manner. In other words, ranges illustrated by the three images are same. Each image illustrated in FIGS. 5A, 5B, and 5C are in black and white for illustration, but in reality, is a color image (same in FIGS. 7A, 7B, and 7C).

Linear shadow region S1 extending in an up-down direction in FIG. 5A corresponds to the crack CR. Shadow region S1a formed in FIG. 5B and shadow region S1b formed in FIG. 5C correspond to shadow regions expressed as arrow AR13 and arrow AR23 in FIGS. 4A and 4B, respectively. When FIGS. 5A and 5C are compared, it is found that the shapes and formation positions of shadow region S1a and shadow region S1b match with each other. In confirmative words, the shapes and formation positions of these two regions also match with shadow region S1 in FIG. 5A.

Figure 6A:
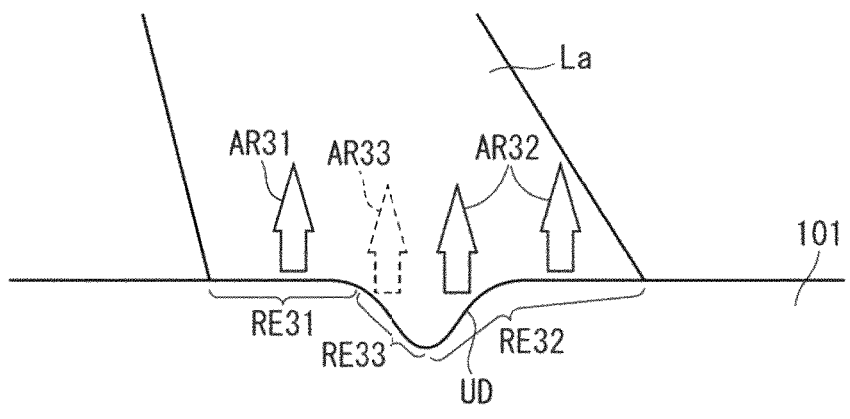
FIGS. 6A and 6B are diagrams for illustration of how an image is formed for a place where an undulation UD is formed on the outer wall 101.
Figure 6B:
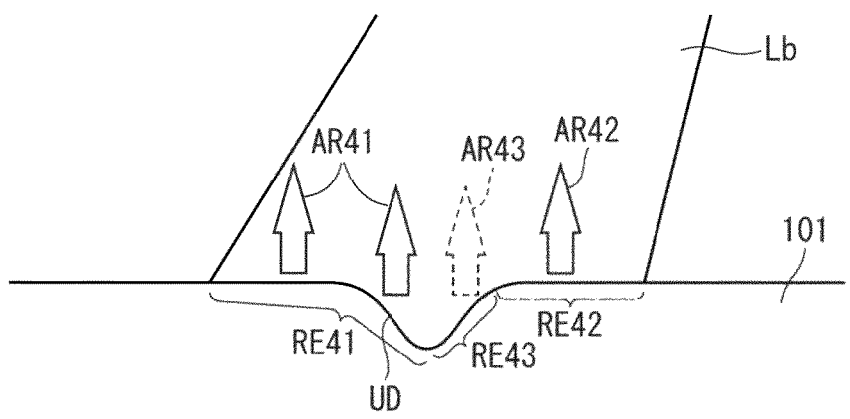

Next, a case in which the undulation UD (concave portion) illustrated as type (c) in FIG. 3 is generated as a deformation will be described. FIGS. 6A and 6B are diagrams for illustration of how an image is formed for a place where the undulation UD is formed on the outer wall 101.

FIG. 6A illustrates how an image is formed with the first illumination light La for the place where the undulation UD is formed. As for regions RE31 and RE32 in which no undulation UD is formed or in which the undulation UD is formed but that face to an illumination direction of the first illumination light La, when the first illumination light La is incident on the surface of the outer wall 101 at the predetermined angle θ as described above, an image of the surface by the first illumination light La is formed at the image capturing means 4 as illustrated with arrow AR31 and arrow AR32.

On the other hand, a region RE33 in which the undulation UD is formed and that does not face to the illumination direction of the first illumination light La does not contribute to image formation by the first illumination light La at the image capturing means 4. In other words, the image capturing means 4 does not obtain an image of the region RE33, and a shadow region is substituted for this region as illustrated with arrow AR33.

Meanwhile, FIG. 6B illustrates how an image is formed with the second illumination light Lb for the place (place same as that in FIG. 6A) where the undulation UD is formed. As for regions RE41 and RE42 in which no undulation UD is formed or in which the undulation UD is formed but that face to an illumination direction of the second illumination light Lb, when the second illumination light Lb is incident on the surface of the outer wall 101 at the predetermined angle θ as described above, an image of the surface by the second illumination light Lb is formed at the image capturing means 4 as illustrated with arrows AR41 and arrow AR42.

On the other hand, a region RE43 in which the undulation UD is formed and that does not face to the illumination direction of the second illumination light Lb does not contribute to image formation by the second illumination light Lb at the image capturing means 4. In other words, the image capturing means 4 does not obtain an image of the region RE43, and a shadow region is substituted for this region as illustrated with arrow AR43.

Figure 7A:
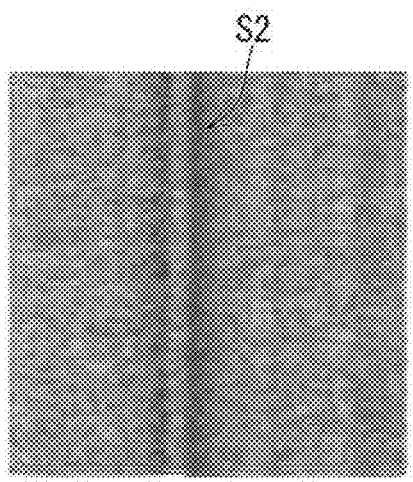
FIGS. 7A, 7B, and 7C are diagrams illustrating images of a place where the undulation UD is formed on the actual outer wall 101.
Figure 7B:
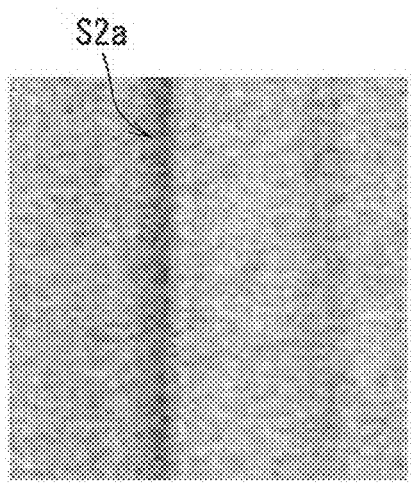
Figure 7C:
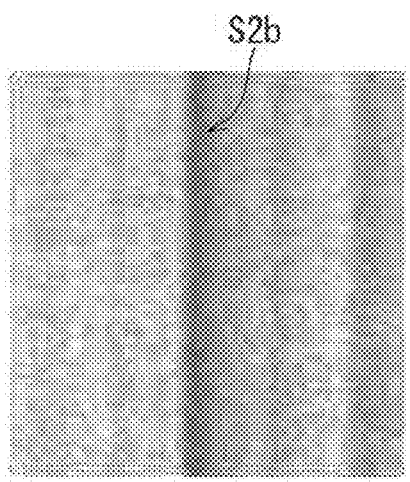

FIGS. 7A, 7B, and 7C are diagrams illustrating images of the place where the undulation UD is formed on the actual outer wall 101. FIG. 7A is a captured image represented by image capturing data obtained by the image capturing means 4, FIG. 7B is an image (the first determination image) represented by the first determination image data generated by the determination image generation part 20 based on the image capturing data that provides the captured image of FIG. 7A, and FIG. 7C is an image (the second determination image) represented by the second determination image data generated in a similar manner. In other words, ranges illustrated by the three images are same.

Linear shadow region S2 extending in an up-down direction in FIG. 7A corresponds to the undulation UD. Shadow region S2a formed in FIG. 7B and shadow region S2b formed in FIG. 7C correspond to shadow regions expressed as arrow AR33 and arrow AR43 in FIGS. 6A and 6B, respectively. When FIGS. 7B and 7C are compared with each other, it is found that the formation positions of shadow region S2a and shadow region S2b do not match with each other. In confirmative words, the formation positions of these two regions are symmetric with respect to shadow region S2 in FIG. 7A.

As described above, with respect to the place where the crack CR is formed and the place where the undulation UD is formed, a shadow region corresponding to the crack CR or the undulation UD is formed in both of the first determination image and the second determination image, but a relation between the formation positions of the shadow regions formed in the two determination images differs between the case with the crack CR and the case with the undulation UD. In other words, when a shadow region is due to the crack CR, the shadow region in the first determination image and the shadow region in the second determination image match with each other, but when a shadow region is due to the undulation UD, the shadow region in the first determination image and the shadow region in the second determination image do not match with each other.

This difference can be obtained due to a difference between formation manners (formation size) of the crack CR and the undulation UD. In schematic words, the crack CR tends to be formed more finely and deeply than the undulation UD.

Figure 8A:
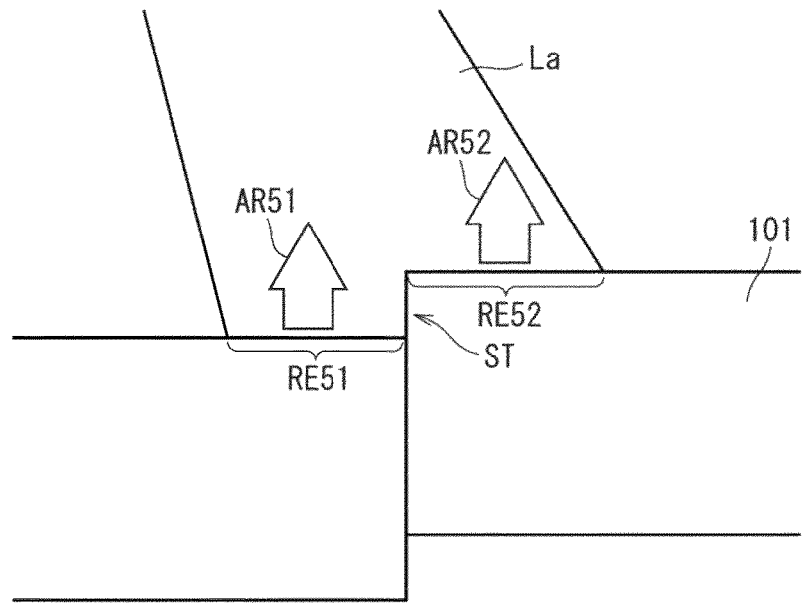
FIGS. 8A and 8B are diagrams for illustration of how an image is formed for a place where a step ST is formed on the outer wall 101.
Figure 8B:
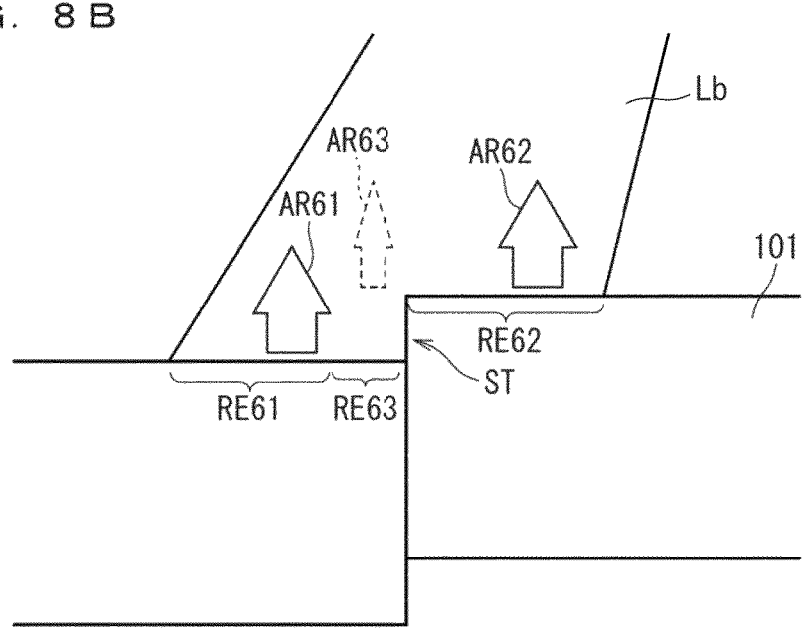

Furthermore, a case in which the step ST illustrated as type (b) in FIG. 3 is generated as a deformation will be described. FIGS. 8A and 8B are diagrams for illustration of how an image is formed for a place where the step ST is formed on the outer wall 101. In FIG. 8, the first illumination light La is emitted from a lower side of the step ST, and the second illumination light Lb is emitted from an upper side of the step ST.

FIG. 8A illustrates how an image is formed with the first illumination light La for the place where the step ST is formed. When the first illumination light La is incident on the surface of the outer wall 101 from the lower side of the step ST at the predetermined angle θ as described above, an image of the surface by the first illumination light La is formed at the image capturing means 4 as illustrated with arrow AR51 and arrow AR52 for regions RE51 and RE52 which are all illumination regions facing to an upper side in FIG. 8A where the image capturing means 4 is disposed. Since any place not illuminated with the first illumination light La does not exist on the surface of the outer wall 101, no shadow region is formed.

Meanwhile, FIG. 8B illustrates how an image is formed with the second illumination light Lb for the place where the step ST is formed (place same as that in FIG. 8A). When the second illumination light Lb is incident on the surface of the outer wall 101 from the upper side of the step ST at the predetermined angle θ as described above, an image of the surface by the first illumination light La is formed at the image capturing means 4 as illustrated with arrows AR61 and AR62 for region RE61 on the lower side of the step ST and far away from the upper side and region RE62 as an illumination region on the upper side of the step ST.

On the other hand, on the lower side of the step ST, a region RE63 not illuminated with the second illumination light Lb is formed near the upper side, and thus the image capturing means 4 does not obtain an image of the region RE63, and a shadow region is substituted for this region as illustrated with arrow AR63.

As a result, although not illustrated, no shadow region is found in the first determination image but a shadow region similarly to shadow region S2b in FIG. 5B is formed in the second determination image in the case that the step ST is formed in a manner illustrated in FIG. 8B. The relation between the formation positions of a shadow region in the first determination image and a shadow region in the second determination image for the step ST is different from any of the relations between the formation positions of a shadow region in the first determination image and a shadow region in the second determination image for the crack CR and the undulation UD described above.

The angle range of the illumination angle θ of the illumination light described above is determined from an assumption that a shadow region for determining each of the crack CR, the undulation UD, and the step ST described above is excellently formed. Specifically, for θ<5°, the positions of two light sources for illumination light are close to each other, and as a result, a shadow region of the step ST cannot be clearly obtained, which is not preferable. In contrast, for θ>30°, shadow regions in the first determination image and the second determination image for the undulation UD overlap with each other, which is not preferable.

The defect determination part 24 determines whether the type of deformation generated on the outer wall 101 is the crack CR, the step ST, or the undulation UD based on a difference in the relation between the formation positions of a shadow region in the first determination image and a shadow region in the second determination image as described above when the first determination image and the second determination image are compared with each other.

In other words, if it is judged that a shadow region extending in a direction (typically, an up-down direction in the first determination image and the second determination image) corresponding to the extrusion direction at the extrusion shaping and having a pixel value smaller than that in a surrounding region exists at identical positions on the outer wall 101 in the first determination image represented by the first determination image data and the second determination image represented by the second determination image data, it is determined that the crack CR has occurred at a place on the outer wall 101 corresponding to the shadow region.

If a shadow region exists in either one of the first determination image and the second determination image but a region corresponding to this shadow region does not exist at the formation position of this shadow region nor near the formation position in the other image, it is determined that the step ST is generated at a place on the outer wall 101 corresponding to this shadow region. In this case, an upper-lower relation of the step can be specified depending on which of the images the shadow region is formed in.

If the similar shadow region exists in both of the first determination image and the second determination image but the formation positions thereof are shifted from each other, it is determined that the undulation UD is generated on the outer wall 101.

As described above, at the determination by the defect determination part 24, a determination criterion of the crack CR and the step ST as the axial direction crack and a determination criterion of the undulation UD are clearly distinguished from each other. Thus, while the axial direction crack is reliably detected, it never happens that the undulation UD is wrongly detected as the axial direction crack. In other words, at the determination by the defect determination part 24, over-detection is excellently prevented from occurring.

Specifically, the defect determination part 24 specifies, for the first determination image data and the second determination image data generated by the determination image generation part 20, a pixel range forming a shadow region in an image (the first determination image or the second determination image) represented by each piece of image data, with a well-known image processing method. In schematic words, a region of continuous pixels each having a pixel value equal to zero or within a predetermined threshold range close to zero is specified as a pixel region corresponding to a shadow region. Then, the first determination image data and the second determination image data are compared to determine whether each shadow region is any one of the crack CR, the step ST, and the undulation UD based on a positional relation between pixel regions corresponding to the shadow region in the image data. Then, when a shadow region determined to be one of the first two exists, the defect determination part 24 determines that the axial direction crack exists, generates determination result data in which pixel position information of the axial direction crack and the type (the crack CR or the step ST) of the axial direction crack are described, and passes the determination result data to the integrated control part 10. The honeycomb structural body 100 for which a determination result having this description content is drawn up is judged to be a disqualified product.

If a pixel region corresponding to a shadow region is not detected in both of the first determination image data and the second determination image data, and if it is determined that only a pixel region corresponding to the undulation UD exists, no axial direction crack is detected, and thus the defect determination part 24 generates determination result data describing that the honeycomb structural body 100 as an inspection target is a qualified product, and passes the determination result data to the integrated control part 10.

As described above, the surface inspecting apparatus according to the present preferred embodiment can more reliably determine the presence or absence of any crack on the side surface (outer wall surface) of a honeycomb structural body than conventionally done, by a simple method involving image capturing using two illumination light having different illumination directions and comparison of two determination images generated based on a result of the image capturing. More specifically, image capturing of the side surface (outer wall surface) of the honeycomb structural body is performed under two illumination light belonging to two wavelength bands different from each other, and subsequently, image data for each of the two wavelength bands from obtained image capturing data is generated, thereafter to reliably determine whether a deformation generated on the outer wall of the honeycomb structural body is a crack along the axial direction or an undulation based on how any shadow region is formed in the two pieces of obtained image data. This allows reliable detection of any crack and avoids false detection of an undulation as a crack, thereby reducing over-detection.

<Modification>

In an inspection method according to the above-described preferred embodiment, the honeycomb structural body 100 having a cylindrical shape is an inspection target, but, according to the principle of the inspection method, a honeycomb structural body as an inspection target does not necessarily need to have a cylindrical shape. For example, when a forward-backward movement mechanism that freely moves the image capturing means 4 forward and backward relative to a honeycomb structural body mounted on the table 2 is provided to the surface inspecting apparatus 1 to allow adjustment of the relative positions of the image capturing means and the honeycomb structural body in accordance with an image capturing position so that the focal length of the image capturing means 4 is maintained, the inspection is possible on a honeycomb structural body shaped in a polygonal column such as a rectangular tube, for example.

Moreover, according to the principle of the inspection method according to the above-described preferred embodiment, the inspection target does not necessarily need to be a honeycomb structural body, but may be any ceramic body shaped in a tube or column that can be mounted on a table. However, based on the capability of excellently performing the determination of a crack and an undulation generated in the axial direction, which is a characteristic of the inspection method, it is preferable that a ceramic fired body manufactured by applying the extrusion molding method is an inspection target.

Alternatively, when a parallel movement mechanism that moves the image capturing means 4 in parallel to a ceramic body mounted on the table 2 is provided to the surface inspecting apparatus 1 to allow adjustment of the relative positions of the image capturing means and the ceramic body in accordance with an image capturing position so that the focal length of the image capturing means 4 is maintained, the inspection is possible on a ceramic body shaped in a flat plate.

Moreover, in the above-described preferred embodiment, the first illumination means 3a and the second illumination means 3b constituting a pair of the illumination means 3 are arranged at positions symmetric with respect to the direction of the normal N of the outer wall 101 of the honeycomb structural body 100, and accordingly, the illumination angles thereof are at the same angle θ, but the arrangement positions of the first illumination means 3a and the second illumination means 3b may be asymmetric with respect to the direction of the normal N as long as the determination of the presence or absence of any crack according to the preferred embodiment can be excellently performed. Thus, the value of the illumination angle θ may differ between the first illumination means 3a and the second illumination means 3b as long as $5° \leq \theta \leq 30°$ is satisfied.

Alternatively, in the above-described preferred embodiment, the image capturing means 4 is arranged on the normal N, but the image capturing means 4 does not necessarily need to be provided precisely on the normal N, and the image capturing means 4 may be arranged at a position substantially matching with the normal or at a position near the normal N as long as the determination of presence or absence of any crack in the above-described preferred embodiment can be excellently performed.

Moreover, in the above-described preferred embodiment, it is exemplarily described that the R image data and the B image data are generated from one piece of continuous image data as the first decomposed image data and the second decomposed image data, but it is possible to directly generate the R image data and the B image data as separate pieces of image data from the start by actually performing illumination only with the first illumination light La and illumination only with the second illumination light Lb and performing image capturing by the image capturing means 4 under each illumination, and to perform the determination processing through the defect determination part 24 by using such the R image data and the B image data. However, in this case, the R image data is obtained by performing image capturing through the image capturing means 4 under illumination only with the first illumination light La while the honeycomb structural body 100 is rotated once about a central axis AX1, and then the B image data is obtained by performing image capturing through the image capturing means 4 under illumination only with the second illumination light Lb while the honeycomb structural body 100 is additionally rotated once about the central axis AX1. Thus, the honeycomb structural body 100 needs to be rotated at least twice. In addition, positioning of both images needs to be accurately performed during the rotation. In this case, if positional shift of the honeycomb structural body 100, fluctuation in the rotational speed thereof, or decentering of a rotational axis thereof occur at the rotation of the honeycomb structural body 100, it is difficult to accurately perform the positioning. Thus, it is evaluated, in terms of a processing efficiency and a determination accuracy, that the processing manner in the above-described preferred embodiment in which image capturing is completed only with one rotation and the R image data and the B image data as data for completely identical positions generated based on single image capturing data are used is more excellent.

Furthermore, the determination processing through the defect determination part 24 can be performed by setting the wavelength bands of two illumination light to be same, making illumination only with the first illumination light La and illumination only with the second illumination light Lb while performing image capturing by the image capturing means 4 under each illumination to generate two pieces of image data corresponding to the R image data and the B image data, and comparing the two pieces of image data.

Moreover, in the above-described preferred embodiment, red light and blue light are used as illumination light and R image data and B image data are generated as decomposed image data, but the wavelength band of the illumination light and a color component (wavelength range thereof) for which the decomposed image data is generated do not necessarily need to match with each other as long as the determination of the presence or absence of any crack can be excellently performed based on a difference between formation manners of shadow regions by comparing two determination images (determination image data). For example, in another aspect, ultraviolet (UV) light and white light may be used as the illumination light, UV image data and R image data may be generated as decomposed image data, and a determination image (determination image data) may be generated based on these pieces of decomposed image data.

Alternatively, in the case that the honeycomb structural body 100 is rotated twice about the central axis AX1, as in the above-described case, such that image capturing is performed at the first rotation under illumination only with the first illumination light La and image capturing is performed at the second rotation under illumination only with the second illumination light Lb, a result of each image capturing may be generated as image capturing data (first and second image capturing data) in a data format in which a brightness value or a luminance value at each pixel is described, first and second determination images (first and second determination image data) may be generated by acquiring the brightness value or the luminance value at each pixel from the image capturing data through the determination image generation part 20, and the presence or absence of any crack on the outer wall 101 of the honeycomb structural body may be checked based on these first and second determination images (first and second determination image data).

Alternatively, in the above-described preferred embodiment, two illumination light having different wavelength bands are used and images used for the determination are in accordance with these bands, but instead, in another aspect, image capturing using two illumination light having different polarization states or image capturing using two illumination light having different phases may be performed, and then a difference in the type of a deformation generated on the outer wall 101 may be specified from an image difference formed by two obtained images.

Moreover, in the above-described preferred embodiment, a result of the determination obtained by the defect determination part 24 is displayed on the display part 7, but in another aspect, instead of performing the determination by the defect determination part 24, two determination images based on two respective pieces of determination image data generated by the determination image generation part 20 may be displayed on the display part 7, and the presence or absence of any crack on the outer wall 101 of a honeycomb structural body may be checked through visual comparison of the two determination images by a worker. When the two determination images are displayed on the display part 7 to allow comparison of a difference between shadow regions existing in the respective two determination images, the determination of the presence or absence of any crack can be performed by a simple method of visual comparison.

Moreover, mainly in the above-described preferred embodiment, the presence or absence of any crack on the outer wall 101 of a honeycomb structural body is checked in such a digital image processing manner that a result of image capturing at the image capturing means 4 is described as pixel values in the image capturing data and passed to the determination image generation part 20 and then determination image data is generated, but instead, in another aspect, the image capturing means 4 may be capable of outputting a result of its image capturing as image formation signals of an analog scheme in a predetermined output format, and the first determination image and the second determination image may be displayed on the display part 7 by using the two image formation signals different from each other among the image formation signals so as to allow comparison of the images. For example, a case in which the image capturing means 4 is capable of outputting an image signal in the RGB format and a first determination image made of an R signal only and a second determination image made of a B signal only are generated is exemplarily described. In this case, too, the presence or absence of any crack on the outer wall 101 of a honeycomb structural body can be checked through visual comparison of the two determination images by a worker.

Alternatively, the determination of the presence or absence of any crack at the defect determination part 24 and the determination of that through the visual comparison of two determination images displayed on the display part 7 by a worker may be both allowed to be performed at the single surface inspecting apparatus 1.

Moreover, in the above-described preferred embodiment, the image capturing means 4 performs image capturing at a timing when an encoder pulse is issued from the rotation mechanism 2*a* that rotates the table 2, but a manner of controlling a timing of the image capturing at the image capturing means 4 is not limited thereto. FIG. 9 is a block diagram of the surface inspecting apparatus 1 that controls the timing of the image capturing at the image capturing means 4 in a manner different from that in the above-described preferred embodiment.

Specifically, at the surface inspecting apparatus 1 illustrated in FIG. 9, control of operation of the image capturing means 4 is performed at an image capturing processing part 14 provided to the control means 5. At this surface inspecting apparatus 1, image capturing by the image capturing means 4 is performed through an image capturing instruction signal provided to the image capturing means 4 from the image capturing processing part 14 based on a control signal from the integrated control part 10.

Moreover, at the surface inspecting apparatus 1 illustrated in FIG. 9, the determination image generation part 20 includes a continuous image generation part 21. The continuous image generation part 21 is a component that performs processing of synthesizing pieces of data of images captured for respective image capturing widths w to generate continuous image data as one piece of captured image data for the entire surface of the outer wall 101.

When the inspection is executed at this surface inspecting apparatus 1, at a stage where rotation operation of the table 2 and an illumination state of illumination light from each of the first illumination means 3*a* and the second illumination means 3*b* have become stable, the integrated control part 10 instructs the image capturing processing part 14 to execute image capturing by the image capturing means 4. In response to this execution instruction, the image capturing processing part 14 causes the image capturing means 4 to perform image capturing at a timing (time interval) set in advance.

Then, when the image capturing is completed for the entire surface of the outer wall 101, the image capturing processing part 14 provides the integrated control part 10 with a signal that gives notification of the completion. Having received this notification signal, the integrated control part 10 provides the rotation control part 12 with an instruction signal to stop the rotation of the rotation mechanism 2*a*, and also provides the illumination control part 13 with an instruction signal to end illumination with the first illumination light La and the second illumination light Lb. When the rotation control part 12 and the illumination control part 13 issue drive signals in response to these instruction signals, the rotation of the table 2 is stopped and the first illumination light La and the second illumination light Lb are turned off.

The image capturing data obtained by the image capturing means 4 are provided sequentially or all at once to the continuous image generation part 21 of the determination image generation part 20 through the image capturing processing part 14.

The continuous image generation part 21 generates continuous image data by synthesizing pieces of image capturing data obtained at sequential image capturing timings, at each acquisition of the image capturing data or all at once after acquisition of all the image capturing data. The generated continuous image data is provided to the decomposed image generation part 22. The subsequent processing is performed in a manner similar to the above-described preferred embodiment.

Alternatively, in another aspect, the image capturing control part 4c may include a timer (not illustrated), and image capturing may be performed at a constant timing by using this timer.

However, the image capturing method according to the above-described preferred embodiment, in which image capturing is performed each time the honeycomb structural body 100 rotates by a constant angle, can reliably capture image capturing of the outer wall 101 even when the honeycomb structural body 100 causes a positional shift at rotation, and thus is more excellent than the methods of controlling an image capturing timing according to these modifications. Also, in the above-described preferred embodiment, image capturing of the entire outer wall 101 of the honeycomb structural body 100 is performed by the single image capturing means 4, but instead, a plurality of the image capturing means 4 may be mounted at a predetermined interval around the honeycomb structural body 100 mounted on the table 2, and the first illumination means 3a and the second illumination means 3b may be provided for each image capturing means 4, so that an image capturing range by the plurality of the image capturing means 4 cover the entire outer wall 101. In this case, image capturing data of the entire outer wall 101 of the honeycomb structural body 100 can be obtained without rotating the table 2.

The invention claimed is:

1. A method of inspecting a crack for a surface of a ceramic body, the method comprising:
   an image capturing step of performing, through a predetermined image capturing means, image capturing of a predetermined illuminated region of an inspection surface which is a partial surface of said ceramic body, said illuminated region being illuminated with at least one of first illumination light and second illumination light;
   a determination image generation step of generating, based on an image capturing result in said image capturing step, a determination image that is usable for determination of the presence or absence of any crack; and
   a determination step of determining the presence or absence of any crack on said inspection surface based on said determination image,
   wherein
   said first and second illumination light is emitted to said inspection surface from mutually different directions sandwiching said image capturing means,
   in said image capturing step, image capturing of said illuminated region is performed under illumination with at least one of said first and second illumination light,
   when a first image capturing result is defined as an image capturing result obtained by performing image capturing of said inspection surface with said image capturing means under illumination at least with said first illumination light, a second image capturing result is defined as an image capturing result obtained by performing image capturing of said inspection surface with said image capturing means under illumination at least with said second illumination light, and in said determination image generation step, a first determination image is generated based on said first image capturing result, and a second determination image is generated based on said second image capturing result, said first and second determination images are generated so that determination of the presence or absence of any crack on said inspection surface can be performed based on a difference between formation manners of shadow regions in said first and second determination images when said first and second determination images are compared with each other, and
   in said determination step, the presence or absence of any crack on said inspection surface is determined based on said first and second determination images,
   wherein in said determination image generation step, said first determination image is generated, based on said first image capturing result, as an image including only an image formation signal for a first color component, or as an image including an image formation signal for said first color component and an image formation signal for a color component other than said first color component, having a signal amount smaller than a predetermined threshold, and
   said second determination image is generated, based on said second image capturing result, as an image including only an image formation signal for a second color component, or an image including an image formation signal for said second color component and an image formation signal for a color component other than said second color component, having a signal amount smaller than a predetermined threshold, and
   wherein in said image capturing step, a result of image capturing with said image capturing means is generated as image capturing data in a predetermined data format,
   said determination image generation step is a determination image data generation step of generating determination image data which is image data of said determination image by acquiring a pixel value for a predetermined color component, as an image formation signal for said predetermined color component, from said image capturing data, and
   in said determination image data generation step, a first determination image data which is image data of said first determination image is generated based on first image capturing data generated as said first image capturing result, and a second determination image data which is image data of said second determination image is generated based on second image capturing data generated as said second image capturing result.

2. The inspection method for the surface of the ceramic body according to claim 1, wherein
   in said image capturing step, a result of image capturing with said image capturing means is generated as image capturing data in a data format in which a pixel value for each of a plurality of color components is independently described, and
   in said determination image data generation step,
   said first determination image data is generated by acquiring, from first image capturing data generated as said first image capturing result, only a pixel value for said first color component, or a pixel value for said first color component and a pixel value for a color component other than said first color component, which is smaller than a predetermined threshold, and
   said second determination image data is generated by acquiring, from second image capturing data generated as said second image capturing result, a pixel value for said second color component, or a pixel value for said second color component and a pixel value for a color component other than said second color component, which is smaller than a predetermined threshold.

3. The inspection method for the surface of the ceramic body according to claim 1, wherein in said image capturing step, a result of image capturing with said image capturing means is generated as image capturing data in a data format in which pieces of pixel value information for a plurality of color components are synthesized, and in said determination image data generation step, said first determination image data in which only a pixel value for said first color component is described, or a pixel value for said first color component and a pixel value for a color component other than said first color component, which is smaller than a predetermined threshold are described, is generated by decomposing first image capturing data generated as said first image capturing result, and said second determination image data in which only a pixel value for said second color component is described, or a pixel value for said second color component and a pixel value for a color component other than said second color component, which is smaller than a predetermined threshold are described, is generated by decomposing second image capturing data generated as said second image capturing result.

4. The inspection method for the surface of the ceramic body according to claim 1, wherein, in said determination step, the presence or absence of any crack on said inspection surface is determined by determining a difference between formation manners of shadow regions in said first and second determination images through comparison of said first and second determination image data, and determination result data in which a result of the determination is described is generated.

5. The inspection method for the surface of the ceramic body according to claim 4, wherein in said determination step, based on said first and second determination image data, when it is judged that a shadow region extending in an identical direction and having a pixel value smaller than a pixel value of a surrounding region exists at identical positions on said inspection surface of said ceramic body in said first and second determination images, and when it is judged said shadow region exists in either one of said first and second determination images, but a region corresponding to said shadow region does not exist at a formation position of said shadow region nor near said formation position in the other determination image, it is determined that a crack along said identical direction is generated at a place corresponding to said shadow region on said inspection surface of said ceramic body.

6. The inspection method for the surface of the ceramic body according to claim 1, wherein a wavelength band of said first illumination light and a wavelength band of said second illumination light are different from each other, in said image capturing step, said first and second image capturing results are acquired as a single image capturing result by performing, with said image capturing means, image capturing of said illuminated region with being illuminated simultaneously with said first and second illumination light, and in said determination image generation step, said first and second determination image data are generated based on said single image capturing result, with setting different wavelength ranges for said first color component and second color component.

7. The inspection method for the surface of the ceramic body according to claim 6, wherein the wavelength range for said first color component overlaps at least with the wavelength band of said first illumination light, and the wavelength range for said second color component overlaps at least with the wavelength band of said second illumination light.

8. The inspection method for the surface of the ceramic body according to claim 6, wherein, in said image capturing step, said single piece of image capturing data is obtained by performing, while said ceramic body is rotated once about a predetermined rotational axis, image capturing with said image capturing means for a surface parallel to said rotational axis as said inspection surface.

9. The inspection method for the surface of the ceramic body according to claim 1, wherein, in said determination image generation step, said first determination image is generated based on a brightness signal or a luminance signal in said first image capturing result, and said second determination image is generated based on a brightness signal or a luminance signal in said second image capturing result.

10. The inspection method for the surface of the ceramic body according to claim 9, wherein in said image capturing step, a result of image capturing with said image capturing means is generated as image capturing data in a data format in which a brightness value or a luminance value at each pixel is described, said determination image generation step is a determination image data generation step of generating determination image data which is image data of said determination image by acquiring a brightness value or a luminance value at each pixel from said image capturing data, and in said determination image data generation step, a first determination image data which is image data of said first determination image is generated based on first image capturing data generated as said first image capturing result, and a second determination image data which is image data of said second determination image is generated based on second image capturing data generated as said second image capturing result.

11. The inspection method for the surface of the ceramic body according to claim 10, wherein, in said determination step, the presence or absence of any crack on said inspection surface is determined by determining a difference between formation manners of shadow regions in said first and second determination images through comparison of said first and second determination image data, and determination result data in which a result of the determination is described is generated.

12. The inspection method for the surface of the ceramic body according to claim 11, wherein in said determination step, based on said first and second determination image data, when it is judged that a shadow region extending in an identical direction and having a pixel value smaller than a pixel value of a surrounding region exists at identical positions on said inspection surface of said ceramic body in said first and second determination images, and when it is judged said shadow region exists in either one of said first and second determination images, but a region corresponding to said shadow region does not exist at a formation position of said shadow region nor near said formation position in the other determination image, it is determined that a crack along said identical direction is generated at a place corresponding to said shadow region on said inspection surface of said ceramic body.

13. The inspection method for the surface of the ceramic body according to claim 1, wherein, in said image capturing step, said first and second image capturing results are obtained by performing, while said ceramic body is rotated about a predetermined rotational axis, image capturing with said image capturing means for a surface parallel to said rotational axis as said inspection surface.

14. The inspection method for the surface of the ceramic body according to claim 13, wherein, in said image capturing step, said first image capturing result is obtained by performing image capturing of an entirety of said inspection surface with said image capturing means under illumination with said first illumination light while said ceramic body is rotated once about said rotational axis, and then said second image capturing result is obtained by performing image capturing of the entirety of said inspection surface with said image capturing means under illumination with said second illumination light while said ceramic body is additionally rotated once about said rotational axis.

15. The inspection method for the surface of the ceramic body according to claim 8, wherein said ceramic body has a cylindrical shape, and in said image capturing step, said ceramic body is held rotatable in a horizontal plane so that a side surface of said ceramic body is said inspection surface.

16. The inspection method for the surface of the ceramic body according to claim 8, wherein in said image capturing step, image capturing of an entirety of said inspection surface is performed by repeatedly performing image capturing with a predetermined image capturing width, with said image capturing means, of said ceramic body rotating about said rotational axis in a manner that respective image capturing ranges are adjacent to each other or partially overlap with each other, and said first and second image capturing results are obtained by synthesizing a plurality of captured images obtained by the repeated image capturing with said image capturing means.

17. The inspection method for the surface of the ceramic body according to claim 16, wherein a line sensor having sensitivity to at least said first and second illumination light is used as said image capturing means.

18. The inspection method for the surface of the ceramic body according to claim 1, further comprising:

an image display step of displaying said first and second determination images on a predetermined image display means to allow determination of the presence or absence of said any crack.

19. The inspection method for the surface of the ceramic body according to claim 18, wherein, in said determination step, the presence or absence of any crack on said inspection surface is determined by determining a difference between formation manners of shadow regions in said first and second determination images through comparison of said first and second determination images displayed on said image display means.

20. The inspection method for the surface of the ceramic body according to claim 19, wherein in said determination step, based on said first and second determination images, when it is judged that a shadow region extending in an identical direction and darker than a surrounding region exists at identical positions on said inspection surface of said ceramic body in said first and second determination images, and when it is judged said shadow region exists in either one of said first and second determination images, but a region corresponding to said shadow region does not exist at a formation position of said shadow region nor near said formation position in the other determination image, it is determined that a crack along said identical direction is generated at a place corresponding to said shadow region on said inspection surface of said ceramic body.

21. The inspection method for the surface of the ceramic body according to claim 1, wherein said first illumination light has a wavelength band of 400 nm to 500 nm, and said second illumination light has a wavelength band of 600 nm to 800 nm.

22. The inspection method for the surface of the ceramic body according to claim 1, wherein said first illumination light has a wavelength band of 100 nm to 400 nm, and said second illumination light has a wavelength band of 300 nm to 800 nm.

23. The inspection method for the surface of the ceramic body according to claim 1, wherein said ceramic body is a honeycomb structural body obtained by firing a ceramic compact obtained by extrusion shaping, and a side surface of said honeycomb structural body is said inspection surface.

24. The inspection method for the surface of the ceramic body according to claim 1, wherein said image capturing step and said determination image generation step are performed by a surface inspecting apparatus comprising a holding part that holds said ceramic body;

first illumination means capable of illuminating said predetermined illuminated region of said ceramic body held by said holding part with said first illumination light;

second illumination means capable of illuminating said predetermined illuminated region of said ceramic body held by said holding part with said second illumination light;

said image capturing means; and a determination image generation means that generates said first determination image based on said first image capturing result and generates said second determination image based on said second image capturing result, said first and second illumination means being arranged with said image capturing means interposed therebetween to illuminate said inspection surface with said first and second illumination light from mutually different directions.

* * * * *